US010191220B2

(12) United States Patent
Kemp

(10) Patent No.: US 10,191,220 B2
(45) Date of Patent: Jan. 29, 2019

(54) POWER-EFFICIENT OPTICAL CIRCUIT

(71) Applicant: VOLCANO CORPORATION, San Diego, CA (US)

(72) Inventor: Nathaniel J. Kemp, Concord, MA (US)

(73) Assignee: VOLCANO CORPORATION, San Diego, CA (US)

( * ) Notice: Subject to any disclaimer, the term of this patent is extended or adjusted under 35 U.S.C. 154(b) by 452 days.

(21) Appl. No.: 14/132,843

(22) Filed: Dec. 18, 2013

(65) Prior Publication Data
US 2014/0178000 A1 Jun. 26, 2014

Related U.S. Application Data

(60) Provisional application No. 61/745,305, filed on Dec. 21, 2012.

(51) Int. Cl.
*G02B 6/35* (2006.01)
*A61B 5/00* (2006.01)
*G02B 6/28* (2006.01)

(52) U.S. Cl.
CPC .......... *G02B 6/354* (2013.01); *A61B 5/0066* (2013.01); *A61B 5/0073* (2013.01); *G02B 6/28* (2013.01); *G02B 6/3592* (2013.01)

(58) Field of Classification Search
CPC .... A61B 5/0066; A61B 5/0073; G02B 6/354; G02B 6/3592; G02B 6/28
USPC ........ 385/14–16, 45; 398/19–10, 14, 16, 79; 600/425, 478
See application file for complete search history.

(56) References Cited

U.S. PATENT DOCUMENTS

| 3,301,258 A | 1/1967 | Werner |
| 3,617,880 A | 11/1971 | Cormack et al. |
| 3,789,841 A | 2/1974 | Antoshkiw |
| 3,841,308 A | 10/1974 | Tate |
| 4,140,364 A | 2/1979 | Yamashita et al. |
| 4,274,423 A | 6/1981 | Mizuno et al. |
| 4,344,438 A | 8/1982 | Schultz |
| 4,398,791 A | 8/1983 | Dorsey |
| 4,432,370 A | 2/1984 | Hughes et al. |
| 4,552,554 A | 11/1985 | Gould et al. |
| 4,577,543 A | 3/1986 | Wilson |
| 4,676,980 A | 6/1987 | Segal et al. |

(Continued)

FOREIGN PATENT DOCUMENTS

| EP | 1041373 A2 | 10/2000 |
| EP | 01172637 A1 | 1/2002 |

(Continued)

OTHER PUBLICATIONS

International Search Report and Written Opinion dated Nov. 2, 2012, for International Patent Application No. PCT/US12/53168, filed Aug. 30, 2013 (8 pages).

(Continued)

*Primary Examiner* — Akm Enayet Ullah

(57) ABSTRACT

The present invention generally relates to optical circuits for mitigating power loss in medical imaging systems and methods for using such circuits. Circuits of the invention can involve a first optical path, a second optical path, and a means for recombining an optical signal transmitted through the first and second optical paths by sequentially gating the first and second optical paths to a single output.

14 Claims, 4 Drawing Sheets

(56) References Cited

U.S. PATENT DOCUMENTS

| | | |
|---|---|---|
| 4,682,895 A | 7/1987 | Costello |
| 4,733,665 A | 3/1988 | Palmaz |
| 4,744,619 A | 5/1988 | Cameron |
| 4,762,129 A | 8/1988 | Bonzel |
| 4,766,386 A | 8/1988 | Oliver et al. |
| 4,771,774 A | 9/1988 | Simpson et al. |
| 4,794,931 A | 1/1989 | Yock |
| 4,800,886 A | 1/1989 | Nestor |
| 4,803,639 A | 2/1989 | Steele et al. |
| 4,816,567 A | 3/1989 | Cabilly et al. |
| 4,819,740 A | 4/1989 | Warrington |
| 4,821,731 A | 4/1989 | Martinelli et al. |
| 4,824,435 A | 4/1989 | Giesy et al. |
| 4,830,023 A | 5/1989 | de Toledo et al. |
| 4,834,093 A | 5/1989 | Littleford et al. |
| 4,841,977 A | 6/1989 | Griffith et al. |
| 4,864,578 A | 9/1989 | Proffitt et al. |
| 4,873,690 A | 10/1989 | Adams |
| 4,877,314 A | 10/1989 | Kanamori |
| 4,887,606 A | 12/1989 | Yock et al. |
| 4,917,085 A | 4/1990 | Smith |
| 4,917,097 A | 4/1990 | Proudian et al. |
| 4,928,693 A | 5/1990 | Goodin et al. |
| 4,932,413 A | 6/1990 | Shockey et al. |
| 4,932,419 A | 6/1990 | de Toledo |
| 4,948,229 A | 8/1990 | Soref |
| 4,951,677 A | 8/1990 | Crowley et al. |
| 4,969,742 A | 11/1990 | Falk et al. |
| 4,987,412 A | 1/1991 | Vaitekunas et al. |
| 4,993,412 A | 2/1991 | Murphy-Chutorian |
| 4,998,972 A | 3/1991 | Chin et al. |
| 5,000,185 A | 3/1991 | Yock |
| 5,024,234 A | 6/1991 | Leary et al. |
| 5,025,445 A | 6/1991 | Anderson et al. |
| 5,032,123 A | 7/1991 | Katz et al. |
| 5,037,169 A | 8/1991 | Chun |
| 5,039,193 A | 8/1991 | Snow et al. |
| 5,040,548 A | 8/1991 | Yock |
| 5,041,108 A | 8/1991 | Fox et al. |
| 5,054,492 A | 10/1991 | Scribner et al. |
| 5,065,010 A | 11/1991 | Knute |
| 5,065,769 A | 11/1991 | de Toledo |
| 5,085,221 A | 2/1992 | Ingebrigtsen et al. |
| 5,095,911 A | 3/1992 | Pomeranz |
| 5,100,424 A | 3/1992 | Jang et al. |
| 5,120,308 A | 6/1992 | Hess |
| 5,125,137 A | 6/1992 | Corl et al. |
| 5,135,486 A | 8/1992 | Eberle et al. |
| 5,135,516 A | 8/1992 | Sahatjian et al. |
| 5,155,439 A | 10/1992 | Holmbo et al. |
| 5,158,548 A | 10/1992 | Lau et al. |
| 5,163,445 A | 11/1992 | Christian et al. |
| 5,167,233 A | 12/1992 | Eberle et al. |
| 5,174,295 A | 12/1992 | Christian et al. |
| 5,176,141 A | 1/1993 | Bom et al. |
| 5,176,674 A | 1/1993 | Hofmann |
| 5,178,159 A | 1/1993 | Christian |
| 5,183,048 A | 2/1993 | Eberle |
| 5,188,632 A | 2/1993 | Goldenberg |
| 5,201,316 A | 4/1993 | Pomeranz et al. |
| 5,202,745 A | 4/1993 | Sorin et al. |
| 5,203,779 A | 4/1993 | Muller et al. |
| 5,220,922 A | 6/1993 | Barany |
| 5,224,953 A | 7/1993 | Morgentaler |
| 5,226,421 A | 7/1993 | Frisbie et al. |
| 5,240,003 A | 8/1993 | Lancee et al. |
| 5,240,437 A | 8/1993 | Christian |
| 5,242,460 A | 9/1993 | Klein et al. |
| 5,243,988 A | 9/1993 | Sieben et al. |
| 5,257,974 A | 11/1993 | Cox |
| 5,266,302 A | 11/1993 | Peyman et al. |
| 5,267,954 A | 12/1993 | Nita |
| 5,301,001 A | 4/1994 | Murphy et al. |
| 5,312,425 A | 5/1994 | Evans et al. |
| 5,313,949 A | 5/1994 | Yock |
| 5,313,957 A | 5/1994 | Little |
| 5,319,477 A * | 6/1994 | DeJule .............. H01Q 3/2676 342/375 |
| 5,319,492 A | 6/1994 | Dorn et al. |
| 5,321,501 A | 6/1994 | Swanson et al. |
| 5,325,198 A | 6/1994 | Hartley et al. |
| 5,331,451 A * | 7/1994 | Mozer .................. H04J 14/08 398/101 |
| 5,336,178 A | 8/1994 | Kaplan et al. |
| 5,346,689 A | 9/1994 | Peyman et al. |
| 5,348,017 A | 9/1994 | Thornton et al. |
| 5,348,481 A | 9/1994 | Ortiz |
| 5,353,798 A | 10/1994 | Sieben |
| 5,358,409 A | 10/1994 | Obara |
| 5,358,478 A | 10/1994 | Thompson et al. |
| 5,368,037 A | 11/1994 | Eberle et al. |
| 5,373,845 A | 12/1994 | Gardineer et al. |
| 5,373,849 A | 12/1994 | Maroney et al. |
| 5,375,602 A | 12/1994 | Lancee et al. |
| 5,377,682 A | 1/1995 | Ueno et al. |
| 5,383,853 A | 1/1995 | Jung et al. |
| 5,387,193 A | 2/1995 | Miraki |
| 5,396,328 A | 3/1995 | Jestel et al. |
| 5,397,355 A | 3/1995 | Marin et al. |
| 5,405,377 A | 4/1995 | Cragg |
| 5,411,016 A | 5/1995 | Kume et al. |
| 5,419,777 A | 5/1995 | Hofling |
| 5,421,338 A | 6/1995 | Crowley et al. |
| 5,423,806 A | 6/1995 | Dale et al. |
| 5,427,118 A | 6/1995 | Nita et al. |
| 5,431,673 A | 7/1995 | Summers et al. |
| 5,436,759 A | 7/1995 | Dijaili et al. |
| 5,439,139 A | 8/1995 | Brovelli |
| 5,443,457 A | 8/1995 | Ginn et al. |
| 5,453,575 A | 9/1995 | O'Donnell et al. |
| 5,456,693 A | 10/1995 | Conston et al. |
| 5,459,570 A | 10/1995 | Swanson et al. |
| 5,480,388 A | 1/1996 | Zadini et al. |
| 5,485,845 A | 1/1996 | Verdonk et al. |
| 5,492,125 A | 2/1996 | Kim et al. |
| 5,496,997 A | 3/1996 | Pope |
| 5,507,761 A | 4/1996 | Duer |
| 5,512,044 A | 4/1996 | Duer |
| 5,514,128 A | 5/1996 | Hillsman et al. |
| 5,529,674 A | 6/1996 | Hedgcoth |
| 5,541,730 A | 7/1996 | Chaney |
| 5,546,717 A | 8/1996 | Penczak et al. |
| 5,546,948 A | 8/1996 | Hamm et al. |
| 5,565,332 A | 10/1996 | Hoogenboom et al. |
| 5,573,520 A | 11/1996 | Schwartz et al. |
| 5,581,638 A | 12/1996 | Givens et al. |
| 5,586,054 A | 12/1996 | Jensen et al. |
| 5,592,939 A | 1/1997 | Martinelli |
| 5,596,079 A | 1/1997 | Smith et al. |
| 5,598,844 A | 2/1997 | Diaz et al. |
| 5,609,606 A | 3/1997 | O'Boyle |
| 5,630,806 A | 5/1997 | Inagaki et al. |
| 5,651,366 A | 7/1997 | Liang et al. |
| 5,660,180 A | 8/1997 | Malinowski et al. |
| 5,667,499 A | 9/1997 | Welch et al. |
| 5,667,521 A | 9/1997 | Keown |
| 5,672,877 A | 9/1997 | Liebig et al. |
| 5,674,232 A | 10/1997 | Halliburton |
| 5,693,015 A | 12/1997 | Walker et al. |
| 5,713,848 A | 2/1998 | Dubrul et al. |
| 5,745,634 A | 4/1998 | Garrett et al. |
| 5,771,895 A | 6/1998 | Slager |
| 5,779,731 A | 7/1998 | Leavitt |
| 5,780,958 A | 7/1998 | Strugach et al. |
| 5,798,521 A | 8/1998 | Froggatt |
| 5,800,450 A | 9/1998 | Lary et al. |
| 5,803,083 A | 9/1998 | Buck et al. |
| 5,814,061 A | 9/1998 | Osborne et al. |
| 5,817,025 A | 10/1998 | Alekseev et al. |
| 5,820,594 A | 10/1998 | Fontirroche et al. |
| 5,824,520 A | 10/1998 | Mulligan-Kehoe |
| 5,827,313 A | 10/1998 | Ream |
| 5,830,222 A | 11/1998 | Makower |

(56) References Cited

U.S. PATENT DOCUMENTS

| | | | |
|---|---|---|---|
| 5,835,199 A * | 11/1998 | Phillips | G01S 7/4802 |
| | | | 356/28.5 |
| 5,848,121 A | 12/1998 | Gupta et al. | |
| 5,851,464 A | 12/1998 | Davila et al. | |
| 5,857,974 A | 1/1999 | Eberle et al. | |
| 5,872,829 A | 2/1999 | Wischmann et al. | |
| 5,873,835 A | 2/1999 | Hastings et al. | |
| 5,882,722 A | 3/1999 | Kydd | |
| 5,912,764 A | 6/1999 | Togino | |
| 5,916,194 A | 6/1999 | Jacobsen et al. | |
| 5,921,931 A | 7/1999 | O'Donnell et al. | |
| 5,925,055 A | 7/1999 | Adrian et al. | |
| 5,946,394 A * | 8/1999 | Gambuzza | H04M 11/06 |
| | | | 379/379 |
| 5,949,929 A | 9/1999 | Hamm | |
| 5,951,586 A | 9/1999 | Berg et al. | |
| 5,974,521 A | 10/1999 | Akerib | |
| 5,976,120 A | 11/1999 | Chow et al. | |
| 5,978,391 A | 11/1999 | Das et al. | |
| 5,997,523 A | 12/1999 | Jang | |
| 6,021,240 A | 2/2000 | Murphy et al. | |
| 6,022,319 A | 2/2000 | Willard et al. | |
| 6,031,071 A | 2/2000 | Mandeville et al. | |
| 6,036,889 A | 3/2000 | Kydd | |
| 6,043,883 A | 3/2000 | Leckel et al. | |
| 6,050,949 A | 4/2000 | White et al. | |
| 6,059,738 A | 5/2000 | Stoltze et al. | |
| 6,068,638 A | 5/2000 | Makower | |
| 6,074,362 A | 6/2000 | Jang et al. | |
| 6,078,831 A | 6/2000 | Belef et al. | |
| 6,080,109 A | 6/2000 | Baker et al. | |
| 6,091,496 A | 7/2000 | Hill | |
| 6,094,591 A | 7/2000 | Foltz et al. | |
| 6,095,976 A | 8/2000 | Nachtomy et al. | |
| 6,097,755 A | 8/2000 | Guenther, Jr. et al. | |
| 6,099,471 A | 8/2000 | Torp et al. | |
| 6,099,549 A | 8/2000 | Bosma et al. | |
| 6,102,938 A | 8/2000 | Evans et al. | |
| 6,106,476 A | 8/2000 | Corl et al. | |
| 6,120,445 A | 9/2000 | Grunwald | |
| 6,123,673 A | 9/2000 | Eberle et al. | |
| 6,134,003 A | 10/2000 | Tearney et al. | |
| 6,139,510 A | 10/2000 | Palermo | |
| 6,141,089 A | 10/2000 | Thoma et al. | |
| 6,146,328 A | 11/2000 | Chiao et al. | |
| 6,148,095 A | 11/2000 | Prause et al. | |
| 6,151,433 A | 11/2000 | Dower et al. | |
| 6,152,877 A | 11/2000 | Masters | |
| 6,152,878 A | 11/2000 | Nachtomy et al. | |
| 6,159,225 A | 12/2000 | Makower | |
| 6,165,127 A | 12/2000 | Crowley | |
| 6,176,842 B1 | 1/2001 | Tachibana et al. | |
| 6,179,809 B1 | 1/2001 | Khairkhahan et al. | |
| 6,186,949 B1 | 2/2001 | Hatfield et al. | |
| 6,190,353 B1 | 2/2001 | Makower et al. | |
| 6,200,266 B1 | 3/2001 | Shokrollahi et al. | |
| 6,200,268 B1 | 3/2001 | Vince et al. | |
| 6,203,537 B1 | 3/2001 | Adrian | |
| 6,208,415 B1 | 3/2001 | De Boer et al. | |
| 6,210,332 B1 | 4/2001 | Chiao et al. | |
| 6,210,339 B1 | 4/2001 | Kiepen et al. | |
| 6,212,308 B1 | 4/2001 | Donald | |
| 6,231,518 B1 | 5/2001 | Grabek et al. | |
| 6,245,066 B1 | 6/2001 | Morgan et al. | |
| 6,249,076 B1 | 6/2001 | Madden et al. | |
| 6,254,543 B1 | 7/2001 | Grunwald et al. | |
| 6,256,090 B1 | 7/2001 | Chen et al. | |
| 6,258,052 B1 | 7/2001 | Milo | |
| 6,261,246 B1 | 7/2001 | Pantages et al. | |
| 6,275,628 B1 | 8/2001 | Jones et al. | |
| 6,278,813 B1 * | 8/2001 | Takada | G02B 6/12011 |
| | | | 385/24 |
| 6,283,921 B1 | 9/2001 | Nix et al. | |
| 6,283,951 B1 | 9/2001 | Flaherty et al. | |
| 6,295,308 B1 | 9/2001 | Zah | |
| 6,299,622 B1 | 10/2001 | Snow et al. | |
| 6,312,384 B1 | 11/2001 | Chiao | |
| 6,325,797 B1 | 12/2001 | Stewart et al. | |
| 6,328,696 B1 | 12/2001 | Fraser | |
| 6,343,168 B1 | 1/2002 | Murphy et al. | |
| 6,343,178 B1 | 1/2002 | Burns et al. | |
| 6,350,240 B1 | 2/2002 | Song et al. | |
| 6,364,841 B1 | 4/2002 | White et al. | |
| 6,366,722 B1 | 4/2002 | Murphy et al. | |
| 6,367,984 B1 | 4/2002 | Stephenson et al. | |
| 6,373,970 B1 | 4/2002 | Dong et al. | |
| 6,375,615 B1 | 4/2002 | Flaherty et al. | |
| 6,375,618 B1 | 4/2002 | Chiao et al. | |
| 6,375,628 B1 | 4/2002 | Zadno-Azizi et al. | |
| 6,376,830 B1 | 4/2002 | Froggatt et al. | |
| 6,379,352 B1 | 4/2002 | Reynolds et al. | |
| 6,381,350 B1 | 4/2002 | Klingensmith et al. | |
| 6,387,124 B1 | 5/2002 | Buscemi et al. | |
| 6,396,976 B1 | 5/2002 | Little et al. | |
| 6,398,792 B1 | 6/2002 | O'Connor | |
| 6,417,948 B1 | 7/2002 | Chowdhury et al. | |
| 6,419,644 B1 | 7/2002 | White et al. | |
| 6,421,164 B2 | 7/2002 | Tearney et al. | |
| 6,423,012 B1 | 7/2002 | Kato et al. | |
| 6,426,796 B1 | 7/2002 | Pulliam et al. | |
| 6,428,041 B1 | 8/2002 | Wohllebe et al. | |
| 6,428,498 B2 | 8/2002 | Uflacker | |
| 6,429,421 B1 | 8/2002 | Meller et al. | |
| 6,440,077 B1 | 8/2002 | Jung et al. | |
| 6,443,903 B1 | 9/2002 | White et al. | |
| 6,450,964 B1 | 9/2002 | Webler | |
| 6,457,365 B1 | 10/2002 | Stephens et al. | |
| 6,459,844 B1 | 10/2002 | Pan | |
| 6,468,290 B1 | 10/2002 | Weldon et al. | |
| 6,475,149 B1 | 11/2002 | Sumanaweera | |
| 6,480,285 B1 | 11/2002 | Hill | |
| 6,491,631 B2 | 12/2002 | Chiao et al. | |
| 6,491,636 B2 | 12/2002 | Chenal et al. | |
| 6,501,551 B1 | 12/2002 | Tearney et al. | |
| 6,504,286 B1 | 1/2003 | Porat et al. | |
| 6,508,824 B1 | 1/2003 | Flaherty et al. | |
| 6,514,237 B1 | 2/2003 | Maseda | |
| 6,520,269 B2 | 2/2003 | Geiger et al. | |
| 6,520,677 B2 | 2/2003 | Iizuka | |
| 6,535,764 B2 | 3/2003 | Imran et al. | |
| 6,538,778 B1 | 3/2003 | Leckel et al. | |
| 6,544,217 B1 | 4/2003 | Gulachenski | |
| 6,544,230 B1 | 4/2003 | Flaherty et al. | |
| 6,545,760 B1 | 4/2003 | Froggatt et al. | |
| 6,546,272 B1 | 4/2003 | MacKinnon et al. | |
| 6,551,250 B2 | 4/2003 | Khalil | |
| 6,566,648 B1 | 5/2003 | Froggatt | |
| 6,570,894 B2 | 5/2003 | Anderson | |
| 6,572,555 B2 | 6/2003 | White et al. | |
| 6,579,311 B1 | 6/2003 | Makower | |
| 6,584,335 B1 | 6/2003 | Haar et al. | |
| 6,592,612 B1 | 7/2003 | Samson et al. | |
| 6,594,448 B2 | 7/2003 | Herman et al. | |
| 6,602,241 B2 | 8/2003 | Makower et al. | |
| 6,611,322 B1 | 8/2003 | Nakayama et al. | |
| 6,611,720 B2 | 8/2003 | Hata et al. | |
| 6,612,992 B1 | 9/2003 | Hossack et al. | |
| 6,615,062 B2 | 9/2003 | Ryan et al. | |
| 6,615,072 B1 | 9/2003 | Izatt et al. | |
| 6,621,562 B2 | 9/2003 | Durston | |
| 6,631,284 B2 | 10/2003 | Nutt et al. | |
| 6,638,227 B2 | 10/2003 | Bae | |
| 6,645,152 B1 | 11/2003 | Jung et al. | |
| 6,646,745 B2 | 11/2003 | Verma et al. | |
| 6,655,386 B1 | 12/2003 | Makower et al. | |
| 6,659,957 B1 | 12/2003 | Vardi et al. | |
| 6,660,024 B1 | 12/2003 | Flaherty et al. | |
| 6,663,565 B2 | 12/2003 | Kawagishi et al. | |
| 6,665,456 B2 | 12/2003 | Dave et al. | |
| 6,669,716 B1 | 12/2003 | Gilson et al. | |
| 6,671,055 B1 | 12/2003 | Wavering et al. | |
| 6,673,015 B1 | 1/2004 | Glover et al. | |
| 6,673,064 B1 | 1/2004 | Rentrop | |
| 6,685,648 B2 | 2/2004 | Flaherty et al. | |

(56) References Cited

U.S. PATENT DOCUMENTS

| | | | |
|---|---|---|---|
| 6,689,056 | B1 | 2/2004 | Kilcoyne et al. |
| 6,689,144 | B2 | 2/2004 | Gerberding |
| 6,696,173 | B1 | 2/2004 | Naundorf et al. |
| 6,701,044 | B2 | 3/2004 | Arbore et al. |
| 6,701,176 | B1 | 3/2004 | Halperin et al. |
| 6,709,444 | B1 | 3/2004 | Makower |
| 6,712,836 | B1 | 3/2004 | Berg et al. |
| 6,714,703 | B2 | 3/2004 | Lee et al. |
| 6,719,717 | B1 | 4/2004 | Johnson et al. |
| 6,725,073 | B1 | 4/2004 | Motamedi et al. |
| 6,726,677 | B1 | 4/2004 | Flaherty et al. |
| 6,730,107 | B2 | 5/2004 | Kelley et al. |
| 6,733,474 | B2 | 5/2004 | Kusleika |
| 6,738,144 | B1 | 5/2004 | Dogariu |
| 6,740,113 | B2 | 5/2004 | Vrba |
| 6,746,464 | B1 | 6/2004 | Makower |
| 6,780,157 | B2 | 8/2004 | Stephens et al. |
| 6,795,188 | B2 | 9/2004 | Ruck et al. |
| 6,795,196 | B2 | 9/2004 | Funakawa |
| 6,798,522 | B2 | 9/2004 | Stolte et al. |
| 6,822,798 | B2 | 11/2004 | Wu et al. |
| 6,823,142 | B1 * | 11/2004 | Tanaka ............... G02B 6/278 359/484.06 |
| 6,830,559 | B2 | 12/2004 | Schock |
| 6,832,024 | B2 | 12/2004 | Gerstenberger et al. |
| 6,842,639 | B1 | 1/2005 | Winston et al. |
| 6,847,449 | B2 | 1/2005 | Bashkansky et al. |
| 6,855,115 | B2 | 2/2005 | Fonseca et al. |
| 6,856,138 | B2 | 2/2005 | Bohley |
| 6,856,400 | B1 | 2/2005 | Froggatt |
| 6,856,472 | B2 | 2/2005 | Herman et al. |
| 6,860,867 | B2 | 3/2005 | Seward et al. |
| 6,866,670 | B2 | 3/2005 | Rabiner et al. |
| 6,878,113 | B2 | 4/2005 | Miwa et al. |
| 6,886,411 | B2 | 5/2005 | Kjellman et al. |
| 6,891,984 | B2 | 5/2005 | Petersen et al. |
| 6,895,106 | B2 | 5/2005 | Wang et al. |
| 6,898,337 | B2 | 5/2005 | Averett et al. |
| 6,900,897 | B2 | 5/2005 | Froggatt |
| 6,912,051 | B2 | 6/2005 | Jensen |
| 6,916,329 | B1 | 7/2005 | Zhao |
| 6,922,498 | B2 | 7/2005 | Shah |
| 6,937,346 | B2 | 8/2005 | Nebendahl et al. |
| 6,937,696 | B1 | 8/2005 | Mostafavi |
| 6,943,939 | B1 | 9/2005 | DiJaili et al. |
| 6,947,147 | B2 | 9/2005 | Motamedi et al. |
| 6,947,787 | B2 | 9/2005 | Webler |
| 6,949,094 | B2 | 9/2005 | Yaron |
| 6,952,603 | B2 | 10/2005 | Gerber et al. |
| 6,954,737 | B2 | 10/2005 | Kalantar et al. |
| 6,958,042 | B2 | 10/2005 | Honda |
| 6,961,123 | B1 | 11/2005 | Wang et al. |
| 6,966,891 | B2 | 11/2005 | Ookubo et al. |
| 6,969,293 | B2 | 11/2005 | Thai |
| 6,969,395 | B2 | 11/2005 | Eskuri |
| 6,985,234 | B2 | 1/2006 | Anderson |
| 7,004,963 | B2 | 2/2006 | Wang et al. |
| 7,006,231 | B2 | 2/2006 | Ostrovsky et al. |
| 7,010,458 | B2 | 3/2006 | Wilt |
| 7,024,025 | B2 | 4/2006 | Sathyanarayana |
| 7,027,211 | B1 | 4/2006 | Ruffa |
| 7,027,743 | B1 | 4/2006 | Tucker et al. |
| 7,033,347 | B2 | 4/2006 | Appling |
| 7,035,484 | B2 | 4/2006 | Silberberg et al. |
| 7,037,269 | B2 | 5/2006 | Nix et al. |
| 7,042,573 | B2 | 5/2006 | Froggatt |
| 7,044,915 | B2 | 5/2006 | White et al. |
| 7,044,964 | B2 | 5/2006 | Jang et al. |
| 7,048,711 | B2 | 5/2006 | Rosenman et al. |
| 7,049,306 | B2 | 5/2006 | Konradi et al. |
| 7,058,239 | B2 | 6/2006 | Singh et al. |
| 7,060,033 | B2 | 6/2006 | White et al. |
| 7,060,421 | B2 | 6/2006 | Naundorf et al. |
| 7,063,679 | B2 | 6/2006 | Maguire et al. |
| 7,068,852 | B2 | 6/2006 | Braica |
| 7,074,188 | B2 | 7/2006 | Nair et al. |
| 7,095,493 | B2 | 8/2006 | Harres |
| 7,110,119 | B2 | 9/2006 | Maestle |
| 7,113,875 | B2 | 9/2006 | Terashima et al. |
| 7,123,777 | B2 | 10/2006 | Rondinelli et al. |
| 7,130,054 | B2 | 10/2006 | Ostrovsky et al. |
| 7,139,440 | B2 | 11/2006 | Rondinelli et al. |
| 7,153,299 | B1 | 12/2006 | Tu et al. |
| 7,171,078 | B2 | 1/2007 | Sasaki et al. |
| 7,175,597 | B2 | 2/2007 | Vince et al. |
| 7,177,491 | B2 | 2/2007 | Dave et al. |
| 7,190,464 | B2 | 3/2007 | Alphonse |
| 7,215,802 | B2 | 5/2007 | Klingensmith et al. |
| 7,218,811 | B2 | 5/2007 | Shigenaga et al. |
| 7,236,812 | B1 | 6/2007 | Ballerstadt et al. |
| 7,245,125 | B2 | 7/2007 | Harer et al. |
| 7,245,789 | B2 | 7/2007 | Bates et al. |
| 7,249,357 | B2 | 7/2007 | Landman et al. |
| 7,291,146 | B2 | 11/2007 | Steinke et al. |
| 7,292,715 | B2 | 11/2007 | Furnish |
| 7,292,885 | B2 | 11/2007 | Scott et al. |
| 7,294,124 | B2 | 11/2007 | Eidenschink |
| 7,300,460 | B2 | 11/2007 | Levine et al. |
| 7,335,161 | B2 | 2/2008 | Von Arx et al. |
| 7,337,079 | B2 | 2/2008 | Park et al. |
| 7,355,716 | B2 | 4/2008 | de Boer et al. |
| 7,356,367 | B2 | 4/2008 | Liang et al. |
| 7,358,921 | B2 | 4/2008 | Snyder et al. |
| 7,359,062 | B2 | 4/2008 | Chen et al. |
| 7,359,554 | B2 | 4/2008 | Klingensmith et al. |
| 7,363,927 | B2 | 4/2008 | Ravikumar |
| 7,366,376 | B2 | 4/2008 | Shishkov et al. |
| 7,382,949 | B2 | 6/2008 | Bouma et al. |
| 7,387,636 | B2 | 6/2008 | Cohn et al. |
| 7,391,520 | B2 | 6/2008 | Zhou et al. |
| 7,397,935 | B2 | 7/2008 | Kimmel et al. |
| 7,399,095 | B2 | 7/2008 | Rondinelli |
| 7,408,648 | B2 | 8/2008 | Kleen et al. |
| 7,414,779 | B2 | 8/2008 | Huber et al. |
| 7,440,087 | B2 | 10/2008 | Froggatt et al. |
| 7,447,388 | B2 | 11/2008 | Bates et al. |
| 7,449,821 | B2 | 11/2008 | Dausch |
| 7,450,165 | B2 | 11/2008 | Ahiska |
| RE40,608 | E | 12/2008 | Glover et al. |
| 7,458,967 | B2 | 12/2008 | Appling et al. |
| 7,463,362 | B2 | 12/2008 | Lasker et al. |
| 7,463,759 | B2 | 12/2008 | Klingensmith et al. |
| 7,491,226 | B2 | 2/2009 | Palmaz et al. |
| 7,515,276 | B2 | 4/2009 | Froggatt et al. |
| 7,527,594 | B2 | 5/2009 | Vardi et al. |
| 7,534,251 | B2 | 5/2009 | WasDyke |
| 7,535,797 | B2 | 5/2009 | Peng et al. |
| 7,547,304 | B2 | 6/2009 | Johnson |
| 7,564,949 | B2 | 7/2009 | Sattler et al. |
| 7,577,471 | B2 | 8/2009 | Camus et al. |
| 7,583,857 | B2 | 9/2009 | Xu et al. |
| 7,603,165 | B2 | 10/2009 | Townsend et al. |
| 7,612,773 | B2 | 11/2009 | Magnin et al. |
| 7,633,627 | B2 | 12/2009 | Choma et al. |
| 7,645,229 | B2 | 1/2010 | Armstrong |
| 7,658,715 | B2 | 2/2010 | Park et al. |
| 7,660,452 | B2 | 2/2010 | Zwirn et al. |
| 7,660,492 | B2 | 2/2010 | Bates et al. |
| 7,666,204 | B2 | 2/2010 | Thornton et al. |
| 7,672,790 | B2 | 3/2010 | McGraw et al. |
| 7,680,247 | B2 | 3/2010 | Atzinger et al. |
| 7,684,991 | B2 | 3/2010 | Stohr et al. |
| 7,711,413 | B2 | 5/2010 | Feldman et al. |
| 7,720,322 | B2 | 5/2010 | Prisco |
| 7,728,986 | B2 | 6/2010 | Lasker et al. |
| 7,734,009 | B2 | 6/2010 | Brunner et al. |
| 7,736,317 | B2 | 6/2010 | Stephens et al. |
| 7,742,795 | B2 | 6/2010 | Stone et al. |
| 7,743,189 | B2 | 6/2010 | Brown et al. |
| 7,762,954 | B2 | 7/2010 | Nix et al. |
| 7,766,896 | B2 | 8/2010 | Kornkven Volk et al. |
| 7,773,792 | B2 | 8/2010 | Kimmel et al. |
| 7,773,883 | B1 * | 8/2010 | Weng ............... H04J 14/0208 398/3 |

(56) References Cited

U.S. PATENT DOCUMENTS

| | | |
|---|---|---|
| 7,775,981 B1 | 8/2010 | Guracar et al. |
| 7,777,399 B2 | 8/2010 | Eidenschink et al. |
| 7,781,724 B2 | 8/2010 | Childers et al. |
| 7,783,337 B2 | 8/2010 | Feldman et al. |
| 7,787,127 B2 | 8/2010 | Galle et al. |
| 7,792,342 B2 | 9/2010 | Barbu et al. |
| 7,801,343 B2 | 9/2010 | Unal et al. |
| 7,801,590 B2 | 9/2010 | Feldman et al. |
| 7,813,609 B2 | 10/2010 | Petersen et al. |
| 7,831,081 B2 | 11/2010 | Li |
| 7,846,101 B2 | 12/2010 | Eberle et al. |
| 7,853,104 B2 | 12/2010 | Oota et al. |
| 7,853,316 B2 | 12/2010 | Milner et al. |
| 7,860,555 B2 | 12/2010 | Saadat |
| 7,862,508 B2 | 1/2011 | Davies et al. |
| 7,872,759 B2 | 1/2011 | Tearney et al. |
| 7,880,868 B2 | 2/2011 | Aoki |
| 7,881,763 B2 | 2/2011 | Brauker et al. |
| 7,909,844 B2 | 3/2011 | Alkhatib et al. |
| 7,921,854 B2 | 4/2011 | Hennings et al. |
| 7,927,784 B2 | 4/2011 | Simpson |
| 7,929,148 B2 | 4/2011 | Kemp |
| 7,930,014 B2 | 4/2011 | Huennekens et al. |
| 7,930,104 B2 | 4/2011 | Baker et al. |
| 7,936,462 B2 | 5/2011 | Jiang et al. |
| 7,942,852 B2 | 5/2011 | Mas et al. |
| 7,947,012 B2 | 5/2011 | Spurchise et al. |
| 7,951,186 B2 | 5/2011 | Eidenschink et al. |
| 7,952,719 B2 | 5/2011 | Brennan, III |
| 7,972,353 B2 | 7/2011 | Hendriksen et al. |
| 7,976,492 B2 | 7/2011 | Brauker et al. |
| 7,977,950 B2 | 7/2011 | Maslen |
| 7,978,916 B2 | 7/2011 | Klingensmith et al. |
| 7,981,041 B2 | 7/2011 | McGahan |
| 7,981,151 B2 | 7/2011 | Rowe |
| 7,983,737 B2 | 7/2011 | Feldman et al. |
| 7,993,333 B2 | 8/2011 | Oral et al. |
| 7,995,210 B2 | 8/2011 | Tearney et al. |
| 7,996,060 B2 | 8/2011 | Trofimov et al. |
| 7,999,938 B2 | 8/2011 | Wang |
| 8,021,377 B2 | 9/2011 | Eskuri |
| 8,021,420 B2 | 9/2011 | Dolan |
| 8,036,732 B2 | 10/2011 | Milner |
| 8,040,586 B2 | 10/2011 | Smith et al. |
| 8,047,996 B2 | 11/2011 | Goodnow et al. |
| 8,049,900 B2 | 11/2011 | Kemp et al. |
| 8,050,478 B2 | 11/2011 | Li et al. |
| 8,050,523 B2 | 11/2011 | Younge et al. |
| 8,052,605 B2 | 11/2011 | Muller et al. |
| 8,057,394 B2 | 11/2011 | Dala-Krishna |
| 8,059,923 B2 | 11/2011 | Bates et al. |
| 8,070,800 B2 | 12/2011 | Lock et al. |
| 8,080,800 B2 | 12/2011 | Hoctor et al. |
| 8,088,102 B2 | 1/2012 | Adams et al. |
| 8,100,838 B2 | 1/2012 | Wright et al. |
| 8,104,479 B2 | 1/2012 | Glynn et al. |
| 8,108,030 B2 | 1/2012 | Castella et al. |
| 8,114,102 B2 | 2/2012 | Galdonik et al. |
| 8,116,605 B2 | 2/2012 | Petersen et al. |
| 8,125,648 B2 | 2/2012 | Milner et al. |
| 8,126,239 B2 | 2/2012 | Sun et al. |
| 8,133,199 B2 | 3/2012 | Weber et al. |
| 8,133,269 B2 | 3/2012 | Flechsenhar et al. |
| 8,140,708 B2 | 3/2012 | Zaharia et al. |
| 8,148,877 B2 | 4/2012 | Jiang et al. |
| 8,167,932 B2 | 5/2012 | Bourang et al. |
| 8,172,757 B2 | 5/2012 | Jaffe et al. |
| 8,177,809 B2 | 5/2012 | Mavani et al. |
| 8,187,191 B2 | 5/2012 | Hancock et al. |
| 8,187,267 B2 | 5/2012 | Pappone et al. |
| 8,187,830 B2 | 5/2012 | Hu et al. |
| 8,199,218 B2 | 6/2012 | Lee et al. |
| 8,206,429 B2 | 6/2012 | Gregorich et al. |
| 8,208,995 B2 | 6/2012 | Tearney et al. |
| 8,222,906 B2 | 7/2012 | Wyar et al. |
| 8,233,681 B2 | 7/2012 | Aylward et al. |
| 8,233,718 B2 | 7/2012 | Klingensmith et al. |
| 8,238,624 B2 | 8/2012 | Doi et al. |
| 8,239,938 B2 | 8/2012 | Simeral et al. |
| 8,277,386 B2 | 10/2012 | Ahmed et al. |
| 8,280,470 B2 | 10/2012 | Milner et al. |
| 8,289,284 B2 | 10/2012 | Glynn et al. |
| 8,289,522 B2 | 10/2012 | Tearney et al. |
| 8,298,147 B2 | 10/2012 | Huennekens et al. |
| 8,298,149 B2 | 10/2012 | Hastings et al. |
| 8,301,000 B2 | 10/2012 | Sillard et al. |
| 8,309,428 B2 | 11/2012 | Lemmerhirt et al. |
| 8,317,713 B2 | 11/2012 | Davies et al. |
| 8,323,201 B2 | 12/2012 | Towfiq et al. |
| 8,329,053 B2 | 12/2012 | Martin et al. |
| 8,336,643 B2 | 12/2012 | Harleman |
| 8,349,000 B2 | 1/2013 | Schreck |
| 8,353,945 B2 | 1/2013 | Andreas et al. |
| 8,353,954 B2 | 1/2013 | Cai et al. |
| 8,357,981 B2 | 1/2013 | Martin et al. |
| 8,361,097 B2 | 1/2013 | Patel et al. |
| 8,386,560 B2 | 2/2013 | Ma et al. |
| 8,398,591 B2 | 3/2013 | Mas et al. |
| 8,412,312 B2 | 4/2013 | Judell et al. |
| 8,417,491 B2 | 4/2013 | Trovato et al. |
| 8,449,465 B2 | 5/2013 | Nair et al. |
| 8,454,685 B2 | 6/2013 | Hariton et al. |
| 8,454,686 B2 | 6/2013 | Alkhatib |
| 8,475,522 B2 | 7/2013 | Jimenez et al. |
| 8,478,384 B2 | 7/2013 | Schmitt et al. |
| 8,486,062 B2 | 7/2013 | Belhe et al. |
| 8,486,063 B2 | 7/2013 | Werneth et al. |
| 8,491,567 B2 | 7/2013 | Magnin et al. |
| 8,500,798 B2 | 8/2013 | Rowe et al. |
| 8,550,911 B2 | 10/2013 | Sylla |
| 8,594,757 B2 | 11/2013 | Boppart et al. |
| 8,597,349 B2 | 12/2013 | Alkhatib |
| 8,600,477 B2 | 12/2013 | Beyar et al. |
| 8,600,917 B1 | 12/2013 | Schimert et al. |
| 8,601,056 B2 | 12/2013 | Lauwers et al. |
| 8,620,055 B2 | 12/2013 | Barratt et al. |
| 8,644,910 B2 | 2/2014 | Rousso et al. |
| 9,075,225 B2 * | 7/2015 | Fine .................. G01N 21/6408 |
| 2001/0007940 A1 | 7/2001 | Tu et al. |
| 2001/0029337 A1 | 10/2001 | Pantages et al. |
| 2001/0037073 A1 | 11/2001 | White et al. |
| 2001/0046345 A1 | 11/2001 | Snyder et al. |
| 2001/0049548 A1 | 12/2001 | Vardi et al. |
| 2002/0034276 A1 | 3/2002 | Hu et al. |
| 2002/0041723 A1 | 4/2002 | Ronnekleiv et al. |
| 2002/0069676 A1 | 6/2002 | Kopp, II et al. |
| 2002/0089335 A1 | 7/2002 | Williams |
| 2002/0099289 A1 | 7/2002 | Crowley |
| 2002/0163646 A1 | 11/2002 | Anderson |
| 2002/0186818 A1 | 12/2002 | Arnaud et al. |
| 2002/0196446 A1 | 12/2002 | Roth et al. |
| 2002/0197456 A1 | 12/2002 | Pope |
| 2003/0004412 A1 | 1/2003 | Izatt et al. |
| 2003/0016604 A1 | 1/2003 | Hanes |
| 2003/0018273 A1 | 1/2003 | Corl et al. |
| 2003/0023153 A1 | 1/2003 | Izatt et al. |
| 2003/0032886 A1 | 2/2003 | Dgany et al. |
| 2003/0050871 A1 | 3/2003 | Broughton |
| 2003/0065371 A1 | 4/2003 | Satake |
| 2003/0069723 A1 | 4/2003 | Hegde |
| 2003/0077043 A1 | 4/2003 | Hamm et al. |
| 2003/0085635 A1 | 5/2003 | Davidsen |
| 2003/0090753 A1 | 5/2003 | Takeyama et al. |
| 2003/0092995 A1 | 5/2003 | Thompson |
| 2003/0093059 A1 | 5/2003 | Griffin et al. |
| 2003/0103212 A1 | 6/2003 | Westphal et al. |
| 2003/0152259 A1 | 8/2003 | Belykh et al. |
| 2003/0181802 A1 | 9/2003 | Ogawa |
| 2003/0187369 A1 | 10/2003 | Lewis et al. |
| 2003/0194165 A1 | 10/2003 | Silberberg et al. |
| 2003/0195419 A1 | 10/2003 | Harada |
| 2003/0208116 A1 | 11/2003 | Liang et al. |
| 2003/0212491 A1 | 11/2003 | Mitchell et al. |
| 2003/0219202 A1 | 11/2003 | Loeb et al. |

(56) References Cited

U.S. PATENT DOCUMENTS

| | | |
|---|---|---|
| 2003/0220749 A1 | 11/2003 | Chen et al. |
| 2003/0228039 A1 | 12/2003 | Green |
| 2004/0015065 A1 | 1/2004 | Panescu et al. |
| 2004/0023317 A1 | 2/2004 | Motamedi et al. |
| 2004/0028333 A1 | 2/2004 | Lomas |
| 2004/0037742 A1 | 2/2004 | Jen et al. |
| 2004/0042066 A1 | 3/2004 | Kinoshita et al. |
| 2004/0054287 A1 | 3/2004 | Stephens |
| 2004/0067000 A1 | 4/2004 | Bates et al. |
| 2004/0068161 A1 | 4/2004 | Couvillon |
| 2004/0082844 A1 | 4/2004 | Vardi et al. |
| 2004/0092830 A1 | 5/2004 | Scott et al. |
| 2004/0106853 A1 | 6/2004 | Moriyama |
| 2004/0111552 A1 | 6/2004 | Arimilli et al. |
| 2004/0126048 A1 | 7/2004 | Dave et al. |
| 2004/0143160 A1 | 7/2004 | Couvillon |
| 2004/0146546 A1 | 7/2004 | Gravett et al. |
| 2004/0186369 A1 | 9/2004 | Lam |
| 2004/0186558 A1 | 9/2004 | Pavcnik et al. |
| 2004/0195512 A1 | 10/2004 | Crosetto |
| 2004/0220606 A1 | 11/2004 | Goshgarian |
| 2004/0225220 A1 | 11/2004 | Rich |
| 2004/0239938 A1 | 12/2004 | Izatt |
| 2004/0242990 A1 | 12/2004 | Brister et al. |
| 2004/0248439 A1 | 12/2004 | Gernhardt et al. |
| 2004/0260236 A1 | 12/2004 | Manning et al. |
| 2005/0013778 A1 | 1/2005 | Green et al. |
| 2005/0031176 A1 | 2/2005 | Hertel et al. |
| 2005/0036150 A1 | 2/2005 | Izatt et al. |
| 2005/0078317 A1 | 4/2005 | Law et al. |
| 2005/0101859 A1 | 5/2005 | Maschke |
| 2005/0140582 A1 | 6/2005 | Lee et al. |
| 2005/0140682 A1 | 6/2005 | Sumanaweera et al. |
| 2005/0140981 A1 | 6/2005 | Waelti |
| 2005/0140984 A1 | 6/2005 | Hitzenberger |
| 2005/0147303 A1 | 7/2005 | Zhou et al. |
| 2005/0165439 A1 | 7/2005 | Weber et al. |
| 2005/0171433 A1 | 8/2005 | Boppart et al. |
| 2005/0171438 A1 | 8/2005 | Chen et al. |
| 2005/0182297 A1 | 8/2005 | Gravenstein et al. |
| 2005/0196028 A1 | 9/2005 | Kleen et al. |
| 2005/0197585 A1 | 9/2005 | Brockway et al. |
| 2005/0213103 A1 | 9/2005 | Everett et al. |
| 2005/0215942 A1 | 9/2005 | Abrahamson et al. |
| 2005/0234445 A1 | 10/2005 | Conquergood et al. |
| 2005/0243322 A1 | 11/2005 | Lasker et al. |
| 2005/0249391 A1 | 11/2005 | Kimmel et al. |
| 2005/0251567 A1 | 11/2005 | Ballew et al. |
| 2005/0254059 A1 | 11/2005 | Alphonse |
| 2005/0264823 A1 | 12/2005 | Zhu et al. |
| 2006/0013105 A1* | 1/2006 | Wada .............. G02B 6/126 369/110.03 |
| 2006/0013523 A1 | 1/2006 | Childers et al. |
| 2006/0015126 A1 | 1/2006 | Sher |
| 2006/0029634 A1 | 2/2006 | Berg et al. |
| 2006/0036167 A1 | 2/2006 | Shina |
| 2006/0038115 A1 | 2/2006 | Maas |
| 2006/0039004 A1 | 2/2006 | de Boer et al. |
| 2006/0041180 A1 | 2/2006 | Viswanathan et al. |
| 2006/0045536 A1* | 3/2006 | Arahira ............ G02F 1/3519 398/152 |
| 2006/0055936 A1 | 3/2006 | Yun et al. |
| 2006/0058622 A1 | 3/2006 | Tearney et al. |
| 2006/0064009 A1 | 3/2006 | Webler et al. |
| 2006/0067620 A1 | 3/2006 | Shishkov et al. |
| 2006/0072808 A1 | 4/2006 | Grimm et al. |
| 2006/0074442 A1 | 4/2006 | Noriega et al. |
| 2006/0098927 A1 | 5/2006 | Schmidt et al. |
| 2006/0100694 A1 | 5/2006 | Globerman |
| 2006/0106375 A1 | 5/2006 | Werneth et al. |
| 2006/0132790 A1 | 6/2006 | Gutin |
| 2006/0135870 A1 | 6/2006 | Webler |
| 2006/0142703 A1 | 6/2006 | Carter et al. |
| 2006/0142733 A1 | 6/2006 | Forsberg |
| 2006/0173299 A1 | 8/2006 | Romley et al. |
| 2006/0179255 A1 | 8/2006 | Yamazaki |
| 2006/0184048 A1 | 8/2006 | Saadat |
| 2006/0187537 A1 | 8/2006 | Huber et al. |
| 2006/0195269 A1 | 8/2006 | Yeatman et al. |
| 2006/0204119 A1 | 9/2006 | Feng et al. |
| 2006/0229591 A1 | 10/2006 | Lee |
| 2006/0239312 A1 | 10/2006 | Kewitsch et al. |
| 2006/0241342 A1 | 10/2006 | Macaulay et al. |
| 2006/0241465 A1 | 10/2006 | Huennekens et al. |
| 2006/0241503 A1 | 10/2006 | Schmitt et al. |
| 2006/0244973 A1 | 11/2006 | Yun et al. |
| 2006/0258895 A1 | 11/2006 | Maschke |
| 2006/0264743 A1 | 11/2006 | Kleen et al. |
| 2006/0267756 A1 | 11/2006 | Kates |
| 2006/0270976 A1 | 11/2006 | Savage et al. |
| 2006/0276709 A1 | 12/2006 | Khamene et al. |
| 2006/0279742 A1 | 12/2006 | Tearney et al. |
| 2006/0279743 A1 | 12/2006 | Boesser et al. |
| 2006/0285638 A1 | 12/2006 | Boese et al. |
| 2006/0287595 A1 | 12/2006 | Maschke |
| 2006/0293597 A1 | 12/2006 | Johnson et al. |
| 2007/0015969 A1 | 1/2007 | Feldman et al. |
| 2007/0016029 A1 | 1/2007 | Donaldson et al. |
| 2007/0016034 A1 | 1/2007 | Donaldson |
| 2007/0016062 A1 | 1/2007 | Park et al. |
| 2007/0027390 A1 | 2/2007 | Maschke et al. |
| 2007/0036417 A1 | 2/2007 | Argiro et al. |
| 2007/0038061 A1 | 2/2007 | Huennekens et al. |
| 2007/0038121 A1 | 2/2007 | Feldman et al. |
| 2007/0038125 A1 | 2/2007 | Kleen et al. |
| 2007/0043292 A1 | 2/2007 | Camus et al. |
| 2007/0043597 A1 | 2/2007 | Donaldson |
| 2007/0049847 A1 | 3/2007 | Osborne |
| 2007/0060973 A1 | 3/2007 | Ludvig et al. |
| 2007/0065077 A1 | 3/2007 | Childers et al. |
| 2007/0066888 A1 | 3/2007 | Maschke |
| 2007/0066890 A1 | 3/2007 | Maschke |
| 2007/0066983 A1 | 3/2007 | Maschke |
| 2007/0084995 A1 | 4/2007 | Newton et al. |
| 2007/0100226 A1 | 5/2007 | Yankelevitz et al. |
| 2007/0135887 A1 | 6/2007 | Maschke |
| 2007/0142707 A1 | 6/2007 | Wiklof et al. |
| 2007/0156019 A1 | 7/2007 | Larkin et al. |
| 2007/0161893 A1 | 7/2007 | Milner et al. |
| 2007/0161896 A1 | 7/2007 | Adachi et al. |
| 2007/0161963 A1 | 7/2007 | Smalling |
| 2007/0162860 A1 | 7/2007 | Muralidharan et al. |
| 2007/0165141 A1 | 7/2007 | Srinivas et al. |
| 2007/0167710 A1 | 7/2007 | Unal et al. |
| 2007/0167804 A1 | 7/2007 | Park et al. |
| 2007/0191682 A1 | 8/2007 | Rolland et al. |
| 2007/0201736 A1 | 8/2007 | Klingensmith et al. |
| 2007/0206193 A1 | 9/2007 | Pesach |
| 2007/0208276 A1 | 9/2007 | Kornkven Volk et al. |
| 2007/0225220 A1 | 9/2007 | Ming et al. |
| 2007/0225590 A1 | 9/2007 | Ramos |
| 2007/0229801 A1 | 10/2007 | Tearney et al. |
| 2007/0232872 A1 | 10/2007 | Prough et al. |
| 2007/0232874 A1 | 10/2007 | Ince |
| 2007/0232890 A1 | 10/2007 | Hirota |
| 2007/0232891 A1 | 10/2007 | Hirota |
| 2007/0232892 A1 | 10/2007 | Hirota |
| 2007/0232893 A1 | 10/2007 | Tanioka |
| 2007/0232933 A1 | 10/2007 | Gille et al. |
| 2007/0238957 A1 | 10/2007 | Yared |
| 2007/0247033 A1 | 10/2007 | Eidenschink et al. |
| 2007/0250000 A1 | 10/2007 | Magnin et al. |
| 2007/0250036 A1 | 10/2007 | Volk et al. |
| 2007/0258094 A1 | 11/2007 | Izatt et al. |
| 2007/0260138 A1 | 11/2007 | Feldman et al. |
| 2007/0278389 A1 | 12/2007 | Ajgaonkar et al. |
| 2007/0287914 A1 | 12/2007 | Cohen |
| 2008/0002183 A1 | 1/2008 | Yatagai et al. |
| 2008/0013093 A1 | 1/2008 | Izatt et al. |
| 2008/0021275 A1 | 1/2008 | Tearney et al. |
| 2008/0027481 A1 | 1/2008 | Gilson et al. |
| 2008/0043024 A1 | 2/2008 | Schiwietz et al. |
| 2008/0045842 A1 | 2/2008 | Furnish |
| 2008/0051660 A1 | 2/2008 | Kakadaris et al. |

(56) References Cited

U.S. PATENT DOCUMENTS

| | | |
|---|---|---|
| 2008/0063304 A1 | 3/2008 | Russak et al. |
| 2008/0085041 A1 | 4/2008 | Breeuwer |
| 2008/0095465 A1 | 4/2008 | Mullick et al. |
| 2008/0095714 A1 | 4/2008 | Castella et al. |
| 2008/0097194 A1 | 4/2008 | Milner |
| 2008/0101667 A1 | 5/2008 | Begelman et al. |
| 2008/0108867 A1 | 5/2008 | Zhou |
| 2008/0114254 A1 | 5/2008 | Matcovitch et al. |
| 2008/0119739 A1 | 5/2008 | Vardi et al. |
| 2008/0124495 A1 | 5/2008 | Horn et al. |
| 2008/0125772 A1 | 5/2008 | Stone et al. |
| 2008/0139897 A1 | 6/2008 | Ainsworth et al. |
| 2008/0143707 A1 | 6/2008 | Mitchell |
| 2008/0146941 A1 | 6/2008 | Dala-Krishna |
| 2008/0147111 A1 | 6/2008 | Johnson et al. |
| 2008/0154128 A1 | 6/2008 | Milner |
| 2008/0161696 A1 | 7/2008 | Schmitt et al. |
| 2008/0171944 A1 | 7/2008 | Brenneman et al. |
| 2008/0175465 A1 | 7/2008 | Jiang et al. |
| 2008/0177183 A1 | 7/2008 | Courtney et al. |
| 2008/0180683 A1 | 7/2008 | Kemp |
| 2008/0181477 A1 | 7/2008 | Izatt et al. |
| 2008/0187201 A1 | 8/2008 | Liang et al. |
| 2008/0228086 A1 | 9/2008 | Ilegbusi et al. |
| 2008/0247622 A1 | 10/2008 | Aylward et al. |
| 2008/0247716 A1 | 10/2008 | Thomas et al. |
| 2008/0262470 A1 | 10/2008 | Lee et al. |
| 2008/0262489 A1 | 10/2008 | Steinke |
| 2008/0269599 A1 | 10/2008 | Csavoy et al. |
| 2008/0281205 A1 | 11/2008 | Naghavi et al. |
| 2008/0281248 A1 | 11/2008 | Angheloiu et al. |
| 2008/0285043 A1 | 11/2008 | Fercher et al. |
| 2008/0287795 A1 | 11/2008 | Klingensmith et al. |
| 2008/0291463 A1 | 11/2008 | Milner et al. |
| 2008/0292173 A1 | 11/2008 | Hsieh et al. |
| 2008/0294034 A1 | 11/2008 | Krueger et al. |
| 2008/0298655 A1 | 12/2008 | Edwards |
| 2008/0306766 A1 | 12/2008 | Ozeki et al. |
| 2009/0009801 A1 | 1/2009 | Tabuki |
| 2009/0018393 A1 | 1/2009 | Dick et al. |
| 2009/0034813 A1 | 2/2009 | Dikmen et al. |
| 2009/0043191 A1 | 2/2009 | Castella et al. |
| 2009/0046295 A1 | 2/2009 | Kemp et al. |
| 2009/0052614 A1 | 2/2009 | Hempel et al. |
| 2009/0069843 A1 | 3/2009 | Agnew |
| 2009/0079993 A1 | 3/2009 | Yatagai et al. |
| 2009/0088650 A1 | 4/2009 | Corl |
| 2009/0093980 A1 | 4/2009 | Kemp et al. |
| 2009/0122320 A1 | 5/2009 | Petersen et al. |
| 2009/0138544 A1 | 5/2009 | Wegenkittl et al. |
| 2009/0149739 A9 | 6/2009 | Maschke |
| 2009/0156941 A1 | 6/2009 | Moore |
| 2009/0174886 A1 | 7/2009 | Inoue |
| 2009/0174931 A1 | 7/2009 | Huber et al. |
| 2009/0177090 A1 | 7/2009 | Grunwald et al. |
| 2009/0177183 A1 | 7/2009 | Pinkernell et al. |
| 2009/0195514 A1 | 8/2009 | Glynn et al. |
| 2009/0195860 A1* | 8/2009 | Arahira ............... G02F 2/004 359/303 |
| 2009/0196470 A1 | 8/2009 | Carl et al. |
| 2009/0198125 A1 | 8/2009 | Nakabayashi et al. |
| 2009/0203991 A1 | 8/2009 | Papaioannou et al. |
| 2009/0264768 A1 | 10/2009 | Courtney et al. |
| 2009/0269014 A1 | 10/2009 | Winberg et al. |
| 2009/0270695 A1 | 10/2009 | McEowen |
| 2009/0284322 A1 | 11/2009 | Harrison et al. |
| 2009/0284332 A1 | 11/2009 | Moore et al. |
| 2009/0284749 A1 | 11/2009 | Johnson et al. |
| 2009/0290167 A1 | 11/2009 | Flanders et al. |
| 2009/0292048 A1 | 11/2009 | Li et al. |
| 2009/0299195 A1 | 12/2009 | Muller et al. |
| 2009/0299284 A1 | 12/2009 | Holman et al. |
| 2009/0318951 A1 | 12/2009 | Kashkarov et al. |
| 2009/0326634 A1 | 12/2009 | Vardi |
| 2010/0007669 A1 | 1/2010 | Bethune et al. |
| 2010/0021166 A1* | 1/2010 | Way ................. H04J 14/02 398/79 |
| 2010/0030042 A1 | 2/2010 | Denninghoff et al. |
| 2010/0061611 A1 | 3/2010 | Xu et al. |
| 2010/0063400 A1 | 3/2010 | Hall et al. |
| 2010/0087732 A1 | 4/2010 | Eberle et al. |
| 2010/0094125 A1 | 4/2010 | Younge et al. |
| 2010/0094127 A1 | 4/2010 | Xu |
| 2010/0094135 A1 | 4/2010 | Fang-Yen et al. |
| 2010/0094143 A1 | 4/2010 | Mahapatra et al. |
| 2010/0113919 A1 | 5/2010 | Maschke |
| 2010/0125238 A1 | 5/2010 | Lye et al. |
| 2010/0125268 A1 | 5/2010 | Gustus et al. |
| 2010/0125648 A1 | 5/2010 | Zaharia et al. |
| 2010/0128348 A1 | 5/2010 | Taverner |
| 2010/0152717 A1 | 6/2010 | Keeler |
| 2010/0160788 A1 | 6/2010 | Davies et al. |
| 2010/0161023 A1 | 6/2010 | Cohen et al. |
| 2010/0168714 A1 | 7/2010 | Burke et al. |
| 2010/0179421 A1 | 7/2010 | Tupin |
| 2010/0179426 A1 | 7/2010 | Davies et al. |
| 2010/0220334 A1 | 9/2010 | Condit et al. |
| 2010/0226607 A1 | 9/2010 | Zhang et al. |
| 2010/0234736 A1 | 9/2010 | Corl |
| 2010/0249601 A1 | 9/2010 | Courtney |
| 2010/0256616 A1 | 10/2010 | Katoh et al. |
| 2010/0272432 A1 | 10/2010 | Johnson |
| 2010/0284590 A1 | 11/2010 | Peng et al. |
| 2010/0290693 A1 | 11/2010 | Cohen et al. |
| 2010/0331950 A1 | 12/2010 | Strommer |
| 2011/0010925 A1 | 1/2011 | Nix et al. |
| 2011/0021926 A1 | 1/2011 | Spencer et al. |
| 2011/0025853 A1 | 2/2011 | Richardson |
| 2011/0026797 A1 | 2/2011 | Declerck et al. |
| 2011/0032533 A1 | 2/2011 | Izatt et al. |
| 2011/0034801 A1 | 2/2011 | Baumgart |
| 2011/0044546 A1 | 2/2011 | Pan et al. |
| 2011/0066073 A1 | 3/2011 | Kuiper et al. |
| 2011/0071401 A1 | 3/2011 | Hastings et al. |
| 2011/0072405 A1 | 3/2011 | Chen et al. |
| 2011/0077528 A1 | 3/2011 | Kemp et al. |
| 2011/0080591 A1 | 4/2011 | Johnson et al. |
| 2011/0087104 A1 | 4/2011 | Moore et al. |
| 2011/0137140 A1 | 6/2011 | Tearney et al. |
| 2011/0144502 A1 | 6/2011 | Zhou et al. |
| 2011/0152771 A1 | 6/2011 | Milner et al. |
| 2011/0157597 A1 | 6/2011 | Lu et al. |
| 2011/0160586 A1 | 6/2011 | Li et al. |
| 2011/0178413 A1 | 7/2011 | Schmitt et al. |
| 2011/0190586 A1 | 8/2011 | Kemp |
| 2011/0216378 A1 | 9/2011 | Poon et al. |
| 2011/0220985 A1 | 9/2011 | Son et al. |
| 2011/0238061 A1 | 9/2011 | van der Weide et al. |
| 2011/0238083 A1 | 9/2011 | Moll et al. |
| 2011/0245669 A1 | 10/2011 | Zhang |
| 2011/0249094 A1 | 10/2011 | Wang et al. |
| 2011/0257545 A1 | 10/2011 | Suri |
| 2011/0264125 A1 | 10/2011 | Wilson et al. |
| 2011/0274329 A1 | 11/2011 | Mathew et al. |
| 2011/0282334 A1 | 11/2011 | Groenhoff |
| 2011/0301684 A1 | 12/2011 | Fischell et al. |
| 2011/0306995 A1 | 12/2011 | Moberg |
| 2011/0319752 A1 | 12/2011 | Steinberg et al. |
| 2012/0004529 A1 | 1/2012 | Tolkowsky et al. |
| 2012/0004668 A1 | 1/2012 | Wallace et al. |
| 2012/0013914 A1 | 1/2012 | Kemp et al. |
| 2012/0016344 A1 | 1/2012 | Kusakabe |
| 2012/0016395 A1 | 1/2012 | Olson |
| 2012/0022360 A1 | 1/2012 | Kemp |
| 2012/0026503 A1 | 2/2012 | Lewandowski et al. |
| 2012/0029007 A1 | 2/2012 | Graham et al. |
| 2012/0059253 A1 | 3/2012 | Wang et al. |
| 2012/0059368 A1 | 3/2012 | Takaoka et al. |
| 2012/0062843 A1 | 3/2012 | Ferguson et al. |
| 2012/0065481 A1 | 3/2012 | Hunter et al. |
| 2012/0071823 A1 | 3/2012 | Chen |
| 2012/0071838 A1 | 3/2012 | Fojtik |
| 2012/0075638 A1 | 3/2012 | Rollins et al. |
| 2012/0083696 A1 | 4/2012 | Kitamura |

(56) References Cited

U.S. PATENT DOCUMENTS

| | | |
|---|---|---|
| 2012/0095340 A1 | 4/2012 | Smith |
| 2012/0095372 A1 | 4/2012 | Sverdlik et al. |
| 2012/0108943 A1 | 5/2012 | Bates et al. |
| 2012/0113108 A1 | 5/2012 | Dala-Krishna |
| 2012/0116353 A1 | 5/2012 | Arnold et al. |
| 2012/0130243 A1 | 5/2012 | Balocco et al. |
| 2012/0130247 A1 | 5/2012 | Waters et al. |
| 2012/0136259 A1 | 5/2012 | Milner et al. |
| 2012/0136427 A1 | 5/2012 | Palmaz et al. |
| 2012/0137075 A1 | 5/2012 | Vorbach |
| 2012/0155734 A1 | 6/2012 | Barratt et al. |
| 2012/0158101 A1 | 6/2012 | Stone et al. |
| 2012/0162660 A1 | 6/2012 | Kemp |
| 2012/0165661 A1 | 6/2012 | Kemp et al. |
| 2012/0170848 A1 | 7/2012 | Kemp et al. |
| 2012/0172698 A1 | 7/2012 | Teo et al. |
| 2012/0176607 A1 | 7/2012 | Ott |
| 2012/0184853 A1 | 7/2012 | Waters |
| 2012/0184859 A1 | 7/2012 | Shah et al. |
| 2012/0184977 A1 | 7/2012 | Wolf |
| 2012/0215094 A1 | 8/2012 | Rahimian et al. |
| 2012/0220836 A1 | 8/2012 | Alpert et al. |
| 2012/0220851 A1 | 8/2012 | Razansky et al. |
| 2012/0220865 A1 | 8/2012 | Brown et al. |
| 2012/0220874 A1 | 8/2012 | Hancock et al. |
| 2012/0220883 A1 | 8/2012 | Manstrom et al. |
| 2012/0224751 A1 | 9/2012 | Kemp et al. |
| 2012/0226153 A1 | 9/2012 | Brown et al. |
| 2012/0230565 A1 | 9/2012 | Steinberg et al. |
| 2012/0230690 A1* | 9/2012 | Doerr ............... G02B 6/12033 398/49 |
| 2012/0232400 A1 | 9/2012 | Dickinson et al. |
| 2012/0238869 A1 | 9/2012 | Schmitt et al. |
| 2012/0238956 A1 | 9/2012 | Yamada et al. |
| 2012/0244043 A1 | 9/2012 | Leblanc et al. |
| 2012/0250028 A1* | 10/2012 | Schmitt ............... G02B 6/2861 356/492 |
| 2012/0253186 A1 | 10/2012 | Simpson et al. |
| 2012/0253192 A1 | 10/2012 | Cressman |
| 2012/0253276 A1 | 10/2012 | Govari et al. |
| 2012/0257210 A1 | 10/2012 | Whitney et al. |
| 2012/0262720 A1 | 10/2012 | Brown et al. |
| 2012/0265077 A1 | 10/2012 | Gille et al. |
| 2012/0265268 A1 | 10/2012 | Blum et al. |
| 2012/0265296 A1 | 10/2012 | McNamara et al. |
| 2012/0271170 A1 | 10/2012 | Emelianov et al. |
| 2012/0271175 A1 | 10/2012 | Moore et al. |
| 2012/0271339 A1 | 10/2012 | O'Beirne et al. |
| 2012/0274338 A1 | 11/2012 | Baks et al. |
| 2012/0276390 A1 | 11/2012 | Ji et al. |
| 2012/0277722 A1 | 11/2012 | Gerber et al. |
| 2012/0279764 A1 | 11/2012 | Jiang et al. |
| 2012/0283758 A1 | 11/2012 | Miller et al. |
| 2012/0289987 A1 | 11/2012 | Wilson et al. |
| 2012/0299439 A1 | 11/2012 | Huang |
| 2012/0310081 A1* | 12/2012 | Adler ............... A61B 5/0035 600/427 |
| 2012/0310332 A1 | 12/2012 | Murray et al. |
| 2012/0319535 A1 | 12/2012 | Dausch |
| 2012/0323075 A1 | 12/2012 | Younge et al. |
| 2012/0323127 A1 | 12/2012 | Boyden et al. |
| 2012/0330141 A1 | 12/2012 | Brown et al. |
| 2013/0015975 A1 | 1/2013 | Huennekens et al. |
| 2013/0023762 A1 | 1/2013 | Huennekens et al. |
| 2013/0023763 A1 | 1/2013 | Huennekens et al. |
| 2013/0026655 A1 | 1/2013 | Lee et al. |
| 2013/0030295 A1 | 1/2013 | Huennekens et al. |
| 2013/0030303 A1 | 1/2013 | Ahmed et al. |
| 2013/0030410 A1 | 1/2013 | Drasler et al. |
| 2013/0053949 A1 | 2/2013 | Pintor et al. |
| 2013/0109958 A1 | 5/2013 | Baumgart et al. |
| 2013/0109959 A1 | 5/2013 | Baumgart et al. |
| 2013/0137980 A1 | 5/2013 | Waters et al. |
| 2013/0150716 A1 | 6/2013 | Stigall et al. |
| 2013/0158594 A1 | 6/2013 | Carrison et al. |
| 2013/0183775 A1* | 7/2013 | Bergmann ........ H01L 27/14601 438/16 |
| 2013/0218201 A1 | 8/2013 | Obermiller et al. |
| 2013/0218267 A1 | 8/2013 | Braido et al. |
| 2013/0223789 A1 | 8/2013 | Lee et al. |
| 2013/0223798 A1 | 8/2013 | Jenner et al. |
| 2013/0296704 A1 | 11/2013 | Magnin et al. |
| 2013/0303907 A1 | 11/2013 | Corl |
| 2013/0303920 A1 | 11/2013 | Corl |
| 2013/0310698 A1 | 11/2013 | Judell et al. |
| 2013/0331820 A1 | 12/2013 | Itou et al. |
| 2013/0338766 A1 | 12/2013 | Hastings et al. |
| 2013/0339958 A1 | 12/2013 | Droste et al. |
| 2014/0039294 A1 | 2/2014 | Jiang |
| 2014/0180067 A1 | 6/2014 | Stigall et al. |
| 2014/0180128 A1 | 6/2014 | Corl |
| 2014/0200438 A1 | 7/2014 | Millett et al. |

FOREIGN PATENT DOCUMENTS

| | | |
|---|---|---|
| EP | 2438877 A2 | 4/2012 |
| GB | 2280261 A | 1/1995 |
| JP | 2000-262461 A | 9/2000 |
| JP | 2000-292260 A | 10/2000 |
| JP | 2001-125009 A | 5/2001 |
| JP | 2001-272331 A | 10/2001 |
| JP | 2002-374034 A | 12/2002 |
| JP | 2003-143783 A | 5/2003 |
| JP | 2003-172690 A | 6/2003 |
| JP | 2003-256876 A | 9/2003 |
| JP | 2003-287534 A | 10/2003 |
| JP | 2005-274380 A | 10/2005 |
| JP | 2006-184284 A | 7/2006 |
| JP | 2006-266797 A | 10/2006 |
| JP | 2006-313158 A | 11/2006 |
| JP | 2007-024677 A | 2/2007 |
| JP | 2009-233001 A | 10/2009 |
| JP | 2011-56786 A | 3/2011 |
| WO | 91/01156 A1 | 2/1991 |
| WO | 92/16865 A1 | 10/1992 |
| WO | 93/06213 A1 | 4/1993 |
| WO | 93/08829 A1 | 5/1993 |
| WO | 98/38907 A1 | 9/1998 |
| WO | 98/57583 A1 | 12/1998 |
| WO | 00/11511 A1 | 3/2000 |
| WO | 00/044296 A1 | 8/2000 |
| WO | 01/11409 A2 | 2/2001 |
| WO | 03/062802 A2 | 7/2003 |
| WO | 03/073950 A1 | 9/2003 |
| WO | 2004/010856 A1 | 2/2004 |
| WO | 2004/023992 A1 | 3/2004 |
| WO | 2004/096049 A2 | 11/2004 |
| WO | 2005/047813 A1 | 5/2005 |
| WO | 2005/106695 A2 | 11/2005 |
| WO | 2006/029634 A2 | 3/2006 |
| WO | 2006/037132 A1 | 4/2006 |
| WO | 2006/039091 A2 | 4/2006 |
| WO | 2006/061829 A1 | 6/2006 |
| WO | 2006/068875 A2 | 6/2006 |
| WO | 2006/111704 A1 | 10/2006 |
| WO | 2006/119416 A2 | 11/2006 |
| WO | 2006/121851 A2 | 11/2006 |
| WO | 2006/130802 A2 | 12/2006 |
| WO | 2007/002685 A2 | 1/2007 |
| WO | 2007/025230 A2 | 3/2007 |
| WO | 2007/045690 A1 | 4/2007 |
| WO | 2007/058895 A2 | 5/2007 |
| WO | 2007/067323 A2 | 6/2007 |
| WO | 2007/084995 A2 | 7/2007 |
| WO | 2008/058084 A2 | 5/2008 |
| WO | 2008/069991 A1 | 6/2008 |
| WO | 2008/107905 A2 | 9/2008 |
| WO | 2009/009799 A1 | 1/2009 |
| WO | 2009/009801 A1 | 1/2009 |
| WO | 2009/046431 A1 | 4/2009 |
| WO | 2009/121067 A1 | 10/2009 |
| WO | 2009/137704 A1 | 11/2009 |
| WO | 2011/06886 A2 | 1/2011 |
| WO | 2011/038048 A1 | 3/2011 |

(56) References Cited

FOREIGN PATENT DOCUMENTS

| | | | |
|---|---|---|---|
| WO | 2011/081688 A1 | 7/2011 |
| WO | 2012/003369 A2 | 1/2012 |
| WO | 2012/061935 A1 | 5/2012 |
| WO | 2012/071388 A2 | 5/2012 |
| WO | 2012/087818 A1 | 6/2012 |
| WO | 2012/098194 A1 | 7/2012 |
| WO | 2012/109676 A1 | 8/2012 |
| WO | 2012/130289 A1 | 10/2012 |
| WO | 2012/154767 A2 | 11/2012 |
| WO | 2012/155040 A1 | 11/2012 |
| WO | 2013/033414 A1 | 3/2013 |
| WO | 2013/033415 A2 | 3/2013 |
| WO | 2013/033418 A1 | 3/2013 |
| WO | 2013/033489 A1 | 3/2013 |
| WO | 2013/033490 A1 | 3/2013 |
| WO | 2013/033592 A1 | 3/2013 |
| WO | 2013/126390 A1 | 8/2013 |
| WO | 2014/109879 A1 | 7/2014 |

OTHER PUBLICATIONS

International Search Report and Written Opinion dated Apr. 14, 2014, for International Patent Application No. PCT/US2013/076148, filed Dec. 18, 2013 (8 pages).
International Search Report and Written Opinion dated Apr. 21, 2014, for International Patent Application No. PCT/US2013/076015, filed Dec. 18, 2013 (7 pages).
International Search Report and Written Opinion dated Apr. 23, 2014, for International Patent Application No. PCT/US2013/075328, filed Dec. 16, 2013 (8 pages).
International Search Report and Written Opinion dated Apr. 29, 2014, for International Patent Application No. PCT/US13/76093, filed Dec. 18, 2013 (6 pages).
International Search Report and Written Opinion dated Apr. 9, 2014, for International Patent Application No. PCT/US13/75089, filed Dec. 13, 2013 (7 pages).
International Search Report and Written Opinion dated Feb. 21, 2014, for International Patent Application No. PCT/US13/76053, filed Dec. 18, 2013 (9 pages).
International Search Report and Written Opinion dated Feb. 21, 2014, for International Patent Application No. PCT/US2013/076965, filed Dec. 20, 2013 (6 pages).
International Search Report and Written Opinion dated Feb. 27, 2014, for International Patent Application No. PCT/US13/75416, filed Dec. 16, 2013 (7 pages).
International Search Report and Written Opinion dated Feb. 28, 2014, for International Patent Application No. PCT/US13/75653, filed Dec. 17, 2013 (7 pages).
International Search Report and Written Opinion dated Feb. 28, 2014, for International Patent Application No. PCT/US13/75990, filed Dec. 18, 2013 (7 pages).
International Search Report and Written Opinion dated Jan. 16, 2009, for International Patent Application No. PCT/US08/78963 filed on Oct. 6, 2008 (7 Pages).
International Search Report and Written Opinion dated Jul. 30, 2014, for International Patent Application No. PCT/US14/21659, filed Mar. 7, 2014 (15 pages).
International Search Report and Written Opinion dated Mar. 10, 2014, for International Patent Application No. PCT/US2013/076212, filed Dec. 18, 2013 (8 pages).
International Search Report and Written Opinion dated Mar. 11, 2014, for International Patent Application No. PCT/US13/76173, filed Dec. 16, 2013 (9 pages).
International Search Report and Written Opinion dated Mar. 11, 2014, for International Patent Application No. PCT/US13/76449, filed Dec. 19, 2013 (9 pages).
International Search Report and Written Opinion dated Mar. 18, 2014, for International Patent Application No. PCT/US2013/076502, filed Dec. 19, 2013 (7 pages).
International Search Report and Written Opinion dated Mar. 18, 2014, for International Patent Application No. PCT/US2013/076788, filed Dec. 20, 2013 (7 pages).
International Search Report and Written Opinion dated Mar. 19, 2014, for International Patent Application No. PCT/US13/75349, filed Dec. 16, 2013 (10 pages).
International Search Report and Written Opinion dated Mar. 19, 2014, for International Patent Application No. PCT/US2013/076587, filed Dec. 19, 2013 (10 pages).
International Search Report and Written Opinion dated Mar. 19, 2014, for International Patent Application No. PCT/US2013/076909, filed Dec. 20, 2013 (7 pages).
International Search Report and Written Opinion dated Mar. 7, 2014, for International Patent Application No. PCT/US2013/076304, filed Dec. 18, 2013 (9 pages).
International Search Report and Written Opinion dated Mar. 7, 2014, for International Patent Application No. PCT/US2013/076480, filed Dec. 19, 2013 (8 pages).
International Search Report and Written Opinion dated Mar. 7, 2014, for International Patent Application No. PCT/US2013/076512, filed Dec. 19, 2013 (8 pages).
International Search Report and Written Opinion dated Mar. 7, 2014, for International Patent Application No. PCT/US2013/076531, filed Dec. 19, 2013 (10 pages).
Jakobovits et al., 1993, Analysis of homozygous mutant chimeric mice:deletion of the immunoglobulin heavy-chain joining region blocks B-cell development and antibody production, PNAS USA 90:2551-255.
Jakobovits et al., 1993, Germ-line transmission and expression of a human-derived yeast artificial chromosome, Nature 362:255-258.
Jang et al., 2002, Visualization of Coronary Atherosclerotic Plaques in Patients Using Optical Coherence Tomography: Comparison With Intravascular Ultrasound, Journal of the American College of Cardiology 39:604-609.
Jiang et al., 1992, Image registration of multimodality 3-D medical images by chamfer matching, Proc. SPIE 1660, Biomedical Image Processing and Three-Dimensional Microscopy, 356-366.
Johnson et al., 1993, Human antibody engineering: Current Opinion in Structural Biology, 3:564-571.
Jones et al., 1986, Replacing the complementarity-determining regions in a human antibody with those from a mouse, Nature, 321:522-525.
Juviler et al., 2008, Anorectal sepsis and fistula-in-ano, Surgical Technology International, 17:139-149.
Karapatis et al., 1998, Direct rapid tooling:a review of current research, Rapid Prototyping Journal, 4(2):77-89.
Karp et al., 2009, The benefit of time-of-flight in PET imaging, J Nucl Med 49:462-470.
Kelly et al., 2005, Detection of Vascular Adhesion Molecule-1 Expression Using a Novel Multimodal Nanoparticle, Circulation Research 96:327-336.
Kemp et al., 2005, Depth Resolved Optic Axis Orientation in Multiple Layered Anisotropic Tissues Measured with Enhanced Polarization Sensitive Optical Coherence Tomography, Optics Express 13(12):4507-4518.
Kersey et al., 1991, Polarization insensitive fiber optic Michelson interferometer, Electron. Lett. 27:518-520.
Kheir et al., 2012, Oxygen Gas-Filled Microparticles Provide Intravenous Oxygen Delivery, Science Translational Medicine 4(140):140ra88 (10 pages).
Khuri-Yakub et al., 2011, Capacitive micromachined ultrasonic transducers for medical imaging and therapy, J Micromech Microeng. 21(5):054004-054014.
Kirkman, 1991, Technique for flow reduction in dialysis access fistulas, Surg Gyn Obstet, 172(3):231-3.
Kohler et al., 1975, Continuous cultures of fused cells secreting antibody of predefined specificity, Nature, 256:495-7.
Koo et al., 2011, Diagnosis of IschemiaCausing Coronary Stenoses by Noninvasive Fractional Flow Reserve Computed From Coronary Computed Tomographic Angiograms, J Am Coll Cardiol 58(19):1989-1997.
Kozbor et al., 1984, A human hybrid myeloma for production of human monoclonal antibodies, J. Immunol., 133:3001-3005.

(56) References Cited

OTHER PUBLICATIONS

Kruth et al., 2003, Lasers and materials in selective laser sintering, Assembly Automation, 23(4):357-371.
Kumagai et al., 1994, Ablation of polymer films by a femtosecond high-peak-power Ti:sapphire laser at 798 nm, Applied Physics Letters, 65(14):1850-1852.
Larin et al., 2002, Noninvasive Blood Glucose Monitoring with Optical Coherence Tomography: a pilot study in human subjects, Diabetes Care, 25(12):2263-7.
Larin et al., 2004, Measurement of Refractive Index Variation of Physiological Analytes using Differential Phase OCT, Proc of SPIE 5325:31-34.
Laufer, 1996, Introduction to Optics and Lasers in Engineering, Cambridge University Press, Cambridge UK:156-162.
Lefevre et al., 2001, Stenting of bifurcation lesions:a rational approach, J. Interv. Cardiol., 14(6):573-585.
Li et al., 2000, Optical Coherence Tomography: Advanced Technology for the Endoscopic Imaging of Barrett's Esophagus, Endoscopy, 32(12):921-930.
Abdi et al., 2010, Principal component analysis, Wiley Interdisciplinary Reviews: Computational Statistics 2:433-459.
Adler et al., 2007, Phase-Sensitive Optical Coherence Tomography at up to 370,000 Lines Per Second Using Buffered Fourier Domain Mode-Locked Lasers, Optics Letters, 32(6):626-628.
Agresti, 1996, Models for Matched Pairs, Chapter 8, An Introduction to Categorical Data Analysis, Wiley-Interscience A John Wiley & Sons, Inc., Publication, Hoboken, New Jersey.
Akasheh et al., 2004, Development of piezoelectric micromachined ultrasonic transducers, Sensors and Actuators A Physical, 111:275-287.
Amini et al., 1990, Using dynamic programming for solving variational problems in vision, IEEE Transactions on Pattern Analysis and Machine Intelligence, 12(9):855-867.
Bail et al., 1996, Optical coherence tomography with the "Spectral Radar"—Fast optical analysis in volume scatterers by short coherence interferometry, Optics Letters 21(14):1087-1089.
Bain, 2011, Privacy protection and face recognition, Chapter 3, Handbook of Face Recognition, Stan et al., Springer-Verlag.
Barnea et al., 1972, A class of algorithms for fast digital image registration, IEEE Trans. Computers, 21(2):179-186.
Blanchet et al., 1993, Laser Ablation and the Production of Polymer Films, Science, 262(5134):719-721.
Bonnema, 2008, Imaging Tissue Engineered Blood Vessel Mimics with Optical Tomography, College of Optical Sciences dissertation, University of Arizona (252 pages).
Bouma et al., 1999, Power-efficient nonreciprocal interferometer and linear-scanning fiber-optic catheter for optical coherence tomography, Optics Letters, 24(8):531-533.
Breiman, 2001, Random forests, Machine Learning 45:5-32.
Brown, 1992, A survey of image registration techniques, ACM Computing Surveys 24(4):325-376.
Bruining et al., 2009, Intravascular Ultrasound Registration/Integration with Coronary Angiography, Cardiology Clinics, 27(3):531-540.
Brummer, 1997, An euclidean distance measure between covariance matrices of speechcepstra for text-independent speaker recognition, in Proc. South African Symp. Communications and Signal Processing:167-172.
Burr et al., 2005, Searching for the Center of an Ellipse in Proceedings of the 17th Canadian Conference on Computational Geometry:260-263.
Canny, 1986, A computational approach to edge detection, IEEE Trans. Pattern Anal. Mach. Intell. 8:679-698.
Cavalli et al., 2010, Nanosponge formulations as oxygen delivery systems, International Journal of Pharmaceutics 402:254-257.
Choma et al., 2003, Sensitivity Advantage of Swept Source and Fourier Domain Optical Coherence Tomography, Optics Express 11(18):2183-2189.
Clarke et al., 1995, Hypoxia and myocardial ischaemia during peripheral angioplasty, Clinical Radiology, 50(5):301-303.

Collins, 1993, Coronary flow reserve, British Heart Journal 69:279-281.
Communication Mechanisms for Distributed Real-Time Applications, NI Developer Zone, http://zone.ni.eom/devzone/cda/tut/p/id/3105, accessed Jul. 23, 2007.
Cook, 2007, Use and misuse of receiver operating characteristic curve in risk prediction, Circulation 115(7):928-35.
D'Agostino et al., 2001, Validation of the Framingham coronary heart disease prediction score: results of a multiple ethnic group investigation, JAMA 286:180-187.
David et al., 1974, Protein iodination with solid-state lactoperoxidase, Biochemistry 13:1014-1021.
Davies et al., 1985, Plaque fissuring—the cause of acute myocardial infarction, sudden ischaemic death, and crescendo angina, British Heart Journal 53:363-373.
Davies et al., 1993, Risk of thrombosis in human atherosclerotic plaques: role of extracellular lipid, macrophage, and smooth muscle cell content, British Heart Journal 69:377-381.
Deterministic Data Streaming in Distributed Data Acquisition Systems, NI Developer Zone, "What is Developer Zone?", http://zone.ni.eom/devzone/cda/tut/p/id/3105, accessed Jul. 23, 2007.
Eigenwillig, 2008, K-Space Linear Fourier Domain Mode Locked Laser and Applications for Optical Coherence Tomography, Optics Express 16(12):8916-8937.
Elghanian et al., 1997, Selective colorimetric detection of polynucleotides based on the distance-dependent optical properties of gold nanoparticles, Science, 277(5329):1078-1080.
Ergun et al., 2003, Capacitive Micromachined Ultrasonic Transducers:Theory and Technology, Journal of Aerospace Engineering, 16(2):76-84.
Evans et al., 2006, Optical coherence tomography to identify intramucosa carcinoma and high-grade dysplasia in Barrett's esophagus, Clin Gast Hepat 4(1):38-43.
Fatemi et al., 1999, Vibro-acoustography: an imaging modality based on ultrasound-stimulated acoustic emission, PNAS U.S.A., 96(12):6603-6608.
Felzenszwalb et al., 2005, Pictorial Structures for Object Recognition, International Journal of Computer Vision, 61(1):55-79.
Ferring et al., 2008, Vasculature ultrasound for the pre-operative evaluation prior to arteriovenous fistula formation for haemodialysis: review of the evidence, Nephrol. Dial. Transplant. 23(6):1809-1815.
Fischler et al., 1973, The representation and matching of pictorial structures, IEEE Transactions on Computer 22:67-92.
Fleming et al., 2010, Real-time monitoring of cardiac radiofrequency ablation lesion formation using an optical coherence tomography forward-imaging catheter, Journal of Biomedical Optics 15 (3):030516-1 (3 pages).
Fookes et al., 2002, Rigid and non-rigid image registration and its association with mutual information:A review, Technical Report ISBN:1 86435 569 7, RCCVA, QUT.
Forstner & Moonen, 1999, A metric for covariance matrices, In Technical Report of the Dpt of Geodesy and Geoinformatics, Stuttgart University, 113-128.
Goel et al., 2006, Minimally Invasive Limited Ligation Endoluminal-assisted Revision (MILLER) for treatment of dialysis access-associated steal syndrome, Kidney Int 70(4):765-70.
Gotzinger et al., 2005, High speed spectral domain polarization sensitive optical coherence tomography of the human retina, Optics Express 13(25):10217-10229.
Gould et al., 1974, Physiologic basis for assessing critical coronary stenosis, American Journal of Cardiology, 33:87-94.
Griffiths et al., 1993, Human anti-self antibodies with high specificity from phage display libraries, The EMBO Journal, 12:725-734.
Griffiths et al., 1994, Isolation of high affinity human antibodies directly from large synthetic repertoires, The EMBO Journal, 13(14):3245-3260.
Grund et al., 2010, Analysis of biomarker data:logs, odds, ratios and ROC curves, Curr Opin HIV AIDS 5(6):473-479.
Harrison et al., 2011, Guidewire Stiffness: What's in a name?, J Endovasc Ther, 18(6):797-801.
Huber et al., 2005, Amplified, Frequency Swept Lasers for Frequency Domain Reflectometry and OCT Imaging: Design and Scaling Principles, Optics Express 13(9):3513-3528.

(56) References Cited

OTHER PUBLICATIONS

Huber et al., 2006, Fourier Domain Mode Locking (FDML): A New Laser Operating Regime and Applications for Optical Coherence Tomography, Optics Express 14(8):3225-3237.
International Search Report and Written Opinion dated Mar. 11, 2014, for International Patent Application No. PCT/US13/75675, filed Dec. 17, 2013 (7 pages).
International Search Report and Written Opinion dated Mar. 19, 2014, for International Patent Application No. PCT/US13/075353, filed Dec. 16, 2013 (8 pages).
Little et al., 1991, The underlying coronary lesion in myocardial infarction:implications for coronary angiography, Clinical Cardiology, 14(11):868-874.
Loo, 2004, Nanoshell Enabled Photonics-Based Imaging and Therapy of Cancer, Technology in Cancer Research & Treatment 3(1):33-40.
Machine translation of JP 2000-097846.
Machine translation of JP 2000-321034.
Machine translation of JP 2000-329534.
Machine translation of JP 2004-004080.
Maintz et al., 1998, An Overview of Medical Image Registration Methods, Technical Report UU-CS, (22 pages).
Mamas et al., 2010, Resting Pd/Pa measured with intracoronary pressure wire strongly predicts fractional flow reserve, Journal of Invasive Cardiology 22(6):260-265.
Marks et al., 1991, By-passing Immunization Human Antibodies from V-gene Libraries Displayed on Phage, J. Mol. Biol. 222:581-597.
Marks et al., 1992, By-Passing Immunization:Building High Affinity Human Antibodies by Chain Shuffling, BioTechnol., 10:779-783.
Maruno et al., 1991, Fluorine containing optical adhesives for optical communications systems, J. Appl. Polymer. Sci. 42:2141-2148.
McCafferty et al., 1990, Phage antibodies: filamentous phage displaying antibody variable domains, Nature 348:552-554.
Mendieta et al., 1996, Complementary sequence correlations with applications to reflectometry studies, Instrumentation and Development 3(6):37-46.
Mickley, 2008, Steal Syndrome—strategies to preserve vascular access and extremity, Nephrol Dial Transplant 23:19-24.
Miller et al., 2010, The MILLER banding procedure is an effective method for treating dialysis-associated steal syndrome, Kidney International 77:359-366.
Milstein et al., 1983, Hybrid hybridomas and their use in immunohistochemistry, Nature 305:537-540.
Mindlin et al., 1936, A force at a point of a semi-infinite solid, Physics, 7:195-202.
Morrison et al., 1984, Chimeric human antibody molecules: mouse antigen-binding domains with human constant region domains, PNAS 81:6851-6855.
Munson et al., 1980, Ligand: a versatile computerized approach for characterization of ligand-binding systems, Analytical Biochemistry, 107:220-239.
Nezam, 2008, High Speed Polygon-Scanner-Based Wavelength-Swept Laser Source in the Telescope-Less Configurations with Application in Optical Coherence Tomography, Optics Letters 33(15):1741-1743.
Nissen, 2001, Coronary Angiography and Intravascular Ultrasound, American Journal of Cardiology, 87 (suppl):15A-20A.
Nitenberg et al., 1995, Coronary vascular reserve in humans: a critical review of methods of evaluation and of interpretation of the results, Eur Heart J. 16(Suppl 1):7-21.
Notice of Reason(s) for Refusal dated Apr. 30, 2013, for Japanese Patent Application No. 2011-508677 for Optical Imaging Catheter for Aberation Balancing to Volcano Corporation, which application is a Japanese national stage entry of PCT/US2009/043181 with international filing date May 7, 2009, of the same title, published on Nov. 12, 2009, as WO 2009/137704, and accompanying English translation of the Notice of Reason(s) for Refusal and machine translation of JP11-56786 and JP2004-290548 (56 pages).
Nygren, 1982, Conjugation of horseradish peroxidase to Fab fragments with different homobifunctional and heterobifunctional cross-linking reagents. A comparative study, J. Histochem. and Cytochem. 30:407-412.
Oesterle et al., 1986, Angioplasty at coronary bifurcations: single-guide, two-wire technique, Cathet Cardiovasc Diagn., 12:57-63.
Okuno et al., 2003, Recent Advances in Optical Switches Using Silica-based PLC Technology, NTT Technical Review 1(7):20-30.
Oldenburg et al., 1998, Nanoengineering of Optical Resonances, Chemical Physics Letters 288:243-247.
Oldenburg et al., 2003, Fast-Fourier-Domain Delay Line for In Vivo Optical Coherence Tomography with a Polygonal Scanner, Applied Optics, 42(22):4606-4611.
Othonos, 1997, Fiber Bragg gratings, Review of Scientific Instruments 68(12):4309-4341.
Owens et al., 2007, A Survey of General-Purpose Computation on Graphics Hardware, Computer Graphics Forum 26(1):80-113.
Pain et al., 1981, Preparation of protein A-peroxidase mono conjugate using a heterobifunctional reagent, and its use in enzyme immunoassays, J Immunol Methods, 40:219-30.
Park et al., 2005, Real-time fiber-based multi-functional spectral-domain optical coherence tomography at 1.3 um., Optics Express 13(11):3931-3944.
Pasquesi et al., 2006, In vivo detection of exercise induced ultrastructural changes in genetically-altered murine skeletal muscle using polarization-sensitive optical coherence tomography, Optics Express 14(4):1547-1556.
Pepe et al., 2004, Limitations of the odds ratio in gauging the performance of a diagnostic, prognostic, or screening marker, American Journal of Epidemiology 159(9):882-890.
Persson et al., 1985, Acoustic impedance matching of medical ultrasound transducers, Ultrasonics, 23(2):83-89.
Placht et al., 2012, Fast time-of-flight camera based surface registration for radiotherapy patient positioning, Medical Physics 39(1):4-17.
Rabbani et al., 1999, Review: Strategies to achieve coronary arterial plaque stabilization, Cardiovascular Research 41:402-417.
Radvany et al., 2008, Plaque Excision in Management of Lower Extremity Peripheral Arterial Disease with the SilverHawk Atherectomy Catheter, Seminars in Interventional Radiology, 25(1):11-19.
Reddy et al., 1996, An FFT-Based Technique for Translation, Rotation, and Scale-Invariant Image Registration, IEEE Transaction on Image Processing 5(8):1266-1271.
Riechmann et al., 1988, Reshaping human antibodies for therapy, Nature, 332:323-327.
Rivers et al., 1992, Correction of steal syndrome secondary to hemodialysis access fistulas: a simplified quantitative technique, Surgery, 112(3):593-7.
Robbin et al., 2002, Hemodialysis Arteriovenous Fistula Maturity: US Evaluation, Radiology 225:59-64.
Rollins et al., 1998, In vivo video rate optical coherence tomography, Optics Express 3:219-229.
Sarunic et al., 2005, Instantaneous Complex Conjugate Resolved Spectral Domain and Swept-Source OCT Using 3×3 Fiber Couplers, Optics Express 13(3):957-967.
Satiani et al., 2009, Predicted Shortage of Vascular Surgeons in the United States, J. Vascular Surgery 50:946-952.
Schneider et al., 2006, T-banding: A technique for flow reduction of a hyper-functioning arteriovenous fistula, J Vasc Surg. 43(2):402-405.
Sen et al., 2012, Development and validation of a new adenosine-independent index of stenosis severity from coronary wave-intensity analysis, Journal of the American College of Cardiology 59(15):1392-1402.
Setta et al., 2005, Soft versus firm embryo transfer catheters for assisted reproduction: a systematic review and meta-analysis, Human Reproduction, 20(11):3114-3121.
Seward et al., 1996, Ultrasound Cardioscopy: Embarking on New Journey, Mayo Clinic Proceedings 71(7):629-635.
Shen et al., 2006, Eigengene-based linear discriminant model for tumor classification using gene expression microarray data, Bioinformatics 22(21):2635-2642.

(56) References Cited

OTHER PUBLICATIONS

Sihan et al., 2008, A novel approach to quantitative analysis of intraluminal optical coherence tomography imaging, Comput. Cardiol:1089-1092.
Siwy et al., 2003, Electro-responsive asymmetric nanopores in polyimide with stable ion-current signal, Applied Physics A: Materials Science & Processing 76:781-785.
Smith et al., 1989, Absolute displacement measurements using modulation of the spectrum of white light in a Michelson interferometer, Applied Optics, 28(16):3339-3342.
Smith, 1997, The Scientist and Engineer's Guide to Digital Signal Processing, California Technical Publishing, San Diego CA:432-436.
Soller, 2003, Polarization diverse optical frequency domain interferometry:All coupler implementation, Bragg Grating, Photosensitivity, and Poling in Glass Waveguides Conference MB4:30-32.
Song et al., 2012, Active tremor cancellation by a "Smart" handheld vitreoretinal microsurgical tool using swept source optical coherence tomography, Optics Express, 20(21):23414-23421.
Stenqvist et al., 1983, Stiffness of central venous catheters, Acta Anaesthesiol Scand., 2:153-157.
Strickland, 1970, Time-Domain Reflectometer Measurements, Tektronix, Beaverton, OR, (107 pages).
Strobl et al., 2009, An Introduction to Recursive Partitioning:Rationale, Application and Characteristics of Classification and Regression Trees, Bagging and Random Forests, Psychol Methods., 14(4):323-348.
Sutcliffe et al., 1986, Dynamics of UV laser ablation of organic polymer surfaces, Journal of Applied Physics, 60(9):3315-3322.
Suzuki, 2013, A novel guidewire approach for handling acute-angle bifurcations, J Inv Cardiol 25(1):48-54.
Tanimoto et al., 2008, A novel approach for quantitative analysis of intracoronary optical coherence tomography: high inter-observer agreement with computer-assisted contour detection, Cathet Cardiovascular Intervent., 72(2):228-235.
Tearney et al., 1997, In vivo Endoscopic Optical Biopsy with Optical Coherence Tomography, Science, 276:2037-2039.
Tonino et al., 2009, Fractional flow reserve versus angiography for guiding percutaneous coronary intervention, The New England Journal of Medicine, 360:213-224.
Toregeani et al., 2008, Evaluation of hemodialysis arteriovenous fistula maturation by color-flow Doppler ultrasound, J Vasc. Bras. 7(3):203-213.
Translation of Notice of Reason(s) for Refusal dated Apr. 30, 2014, for Japanese Patent Application No. 2011-508677, (5 pages).
Translation of Notice of Reason(s) for Refusal dated May 25, 2012, for Japanese Patent Application No. 2009-536425, (3 pages).
Translation of Notice of Reason(s) for Refusal dated Nov. 22, 2012, for Japanese Patent Application No. 2010-516304, (6 pages).
Traunecker et al., 1991, Bispecific single chain molecules (Janusins) target cytotoxic lymphocytes on HIV infected cells, EMBO J., 10:3655-3659.
Trolier-McKinstry et. al., 2004, Thin Film Piezoelectric for MEMS, Journal of Electroceramics 12:7-17.
Tuniz et al., 2010, Weaving the invisible thread: design of an optically invisible metamaterial fibre, Optics Express 18(17):18095-18105.
Turk et al., 1991, Eigenfaces for Recognition, Journal of Cognitive Neuroscience 3(1):71-86.
Tuzel et al., 2006, Region Covariance: A Fast Descriptor for Detection and Classification, European Conference on Computer Vision (ECCV).
Urban et al., 2010, Design of a Pressure Sensor Based on Optical Bragg Grating Lateral Deformation, Sensors (Basel), 10(12):11212-11225.
Vakhtin et al., 2003, Common-path interferometer for frequency-domain optical coherence tomography, Applied Optics, 42(34):6953-6958.
Vakoc et al., 2005, Phase-Resolved Optical Frequency Domain Imaging, Optics Express 13(14):5483-5493.
Verhoeyen et al., 1988, Reshaping human antibodies: grafting an antilysozyme activity, Science, 239:1534-1536.
Villard et al., 2002, Use of a blood substitute to determine instantaneous murine right ventricular thickening with optical coherence tomography, Circulation, 105:1843-1849.
Wang et al., 2002, Optimizing the Beam Patten of a Forward-Viewing Ring-Annular Ultrasound Array for Intravascular Imaging, Transactions on Ultrasonics, Ferroelectrics, and Frequency Control, 49(12).
Wang et al., 2006, Multiple biomarkers for the prediction of first major cardiovascular events and death, The New England Journal of Medicine, 355(25):2631-2639.
Wang et al., 2009, Robust Guidewire Tracking in Fluoroscopy, IEEE Conference on Computer Vision and Pattern Recognition—CVPR 2009:691-698.
Wang et al., 2011, In vivo intracardiac optical coherence tomography imaging through percutaneous access: toward image-guided radio-frequency ablation, J. Biomed. Opt. 0001 16(11):110505-1 (3 pages).
Waterhouse et. al., 1993, Combinatorial infection and in vivo recombination: a strategy for making large phage antibody repertoires, Nucleic Acids Res., 21:2265-2266.
Wegener, 2011, 3D Photonic Metamaterials and Invisibility Cloaks: The Method of Making, MEMS 2011, Cancun, Mexico, Jan. 23-27, 2011.
West et al., 1991, Arterial insufficiency in hemodialysis access procedures: correction by banding technique, Transpl Proc 23(2):1838-40.
Wyawahare et al., 2009, Image registration techniques: an overview, International Journal of Signal Processing, Image Processing and Pattern Recognition, 2(3):11-28.
Yaqoob et al., 2006, Methods and application areas of endoscopic optical coherence tomography, J. Biomed. Opt., 11, 063001-1-063001-19.
Yasuno et al., 2004, Polarization-sensitive complex Fourier domain optical coherence tomography for Jones matrix imaging of biological samples, Applied Physics Letters 85(15):3023-3025.
Zhang et al., 2004, Full range polarization-sensitive Fourier domain optical coherence tomography, Optics Express, 12(24):6033-6039.
Zitova et al., 2003, Image registration methods: A survey. Image and Vision Computing, 21(11):977-1000.

\* cited by examiner

POWER-EFFICIENT OPTICAL CIRCUIT

CROSS-REFERENCE TO RELATED APPLICATION

This application claims priority to, and the benefit of, U.S. Provisional Patent Application Ser. No. 61/745,305, filed Dec. 21, 2012, the contents of which are incorporated by reference.

FIELD OF THE INVENTION

The present invention generally relates to optical circuits for mitigating power loss in medical imaging systems.

BACKGROUND

Optical coherence tomography (OCT) is a medical imaging technique that uses reflected light to produce an image. In OCT, light from a broadband light source is split by an optical fiber splitter with one fiber directing light to a sample path and the other fiber directing light to a reference path mirror. An end of the sample path is typically connected to a scanning device. The light reflected from the scanning device is recombined with the signal from the reference mirror to form interference fringes, which are transformed into a depth-resolved image. In swept-source OCT, the interference spectrum is recorded using a source with an adjustable optical frequency, in which the optical frequency is swept through a range of frequencies and the interfered light intensity is recorded as a function of time during the sweep.

Optical buffering, as used in swept-source OCT, is a method to copy, induce a relative delay (i.e., a buffer), and then recombine two or more optical signals in order to increase the effective imaging speed beyond that of the native imaging speed of the light source.

Traditionally, the buffering approach works by splitting the light source optical signal into multiple paths, delaying the signals with respect to each other, and then recombining the relatively delayed signals using an optical coupler into a common path for subsequent introduction into the OCT system. With this approach, imaging speed has been increased by as much as 16-fold over the native transmission speed of the light source.

The recombination of optically buffered signals using the typical 50/50 coupler, however, discards half of the optical power present in each light source sweep. This unfortunately leads to a reduction in overall system sensitivity. Moreover, the loss in power comprises image quality and has a negative impact on signal-to-noise.

SUMMARY

The present invention provides optical circuits that include an optical switch for recombining buffered and non-buffered optical signals transmitted through the optical circuit. The optical switch toggles between buffered and non-buffered signals in an alternating fashion and redirects each signal to a single output. As encompassed by the invention, the optical switch contains two input ports and a single output port. One input port is connected to an optical path transmitting the buffered signal and the other input port is connected to a second optical path transmitting the non-buffered signal. As the switch toggles back and forth, the switch allows the signal from one optical path to pass while preventing passage of the other signal. Each signal, however, is directed to the single output port of the optical switch. Because the entire buffered and non-buffered signal is directed to a single output, no power is lost during the recombination process.

Due to the optical switch, optical circuits of the invention provide better signal-to-noise ratios than conventional buffering circuits that use optical couplers for recombining signals. The improved signal-to-noise leads to sharper resolution and better imaging when the provided circuits are used in conjunction with various imaging methods. Although any imaging method is useful, the provided circuits are particularly amenable for use in optical coherence tomography (OCT), wherein reflected light is used to obtain depth-resolved images. Circuits of the invention can be used with OCT imaging devices, such as OCT imaging catheters, to obtain high-quality intravascular images.

In addition to the provided optical circuits, the invention also encompasses methods for reducing power loss in an optical circuit. The provided methods involve recombining optical signals transmitted through multiple paths of an optical circuit by sequentially gating the multiple paths to a single output, thereby reducing power loss in the optical circuit. Methods of the invention utilize an optical switch that redirects light from any of the input ports connected to the optical paths to a single output port in a sequential fashion, as explained above.

Circuits and methods of the invention are useful in a variety of optical buffering configurations. For example, the invention is equally applicable to buffering approaches with higher multiplication factors (i.e., 4×, 8×, 16×, etc.). Circuits and methods of the invention are also applicable to polarization-maintaining (PM) buffering schemes. In this aspect, the invention would use PM optical switches and fibers rather than standard optical switches and single mode fibers. Circuits and methods of the invention are also useful with a variety of delay approaches, such as single-pass, double-pass, and quad-pass delay schemes.

DETAILED DESCRIPTION

Figure 1:
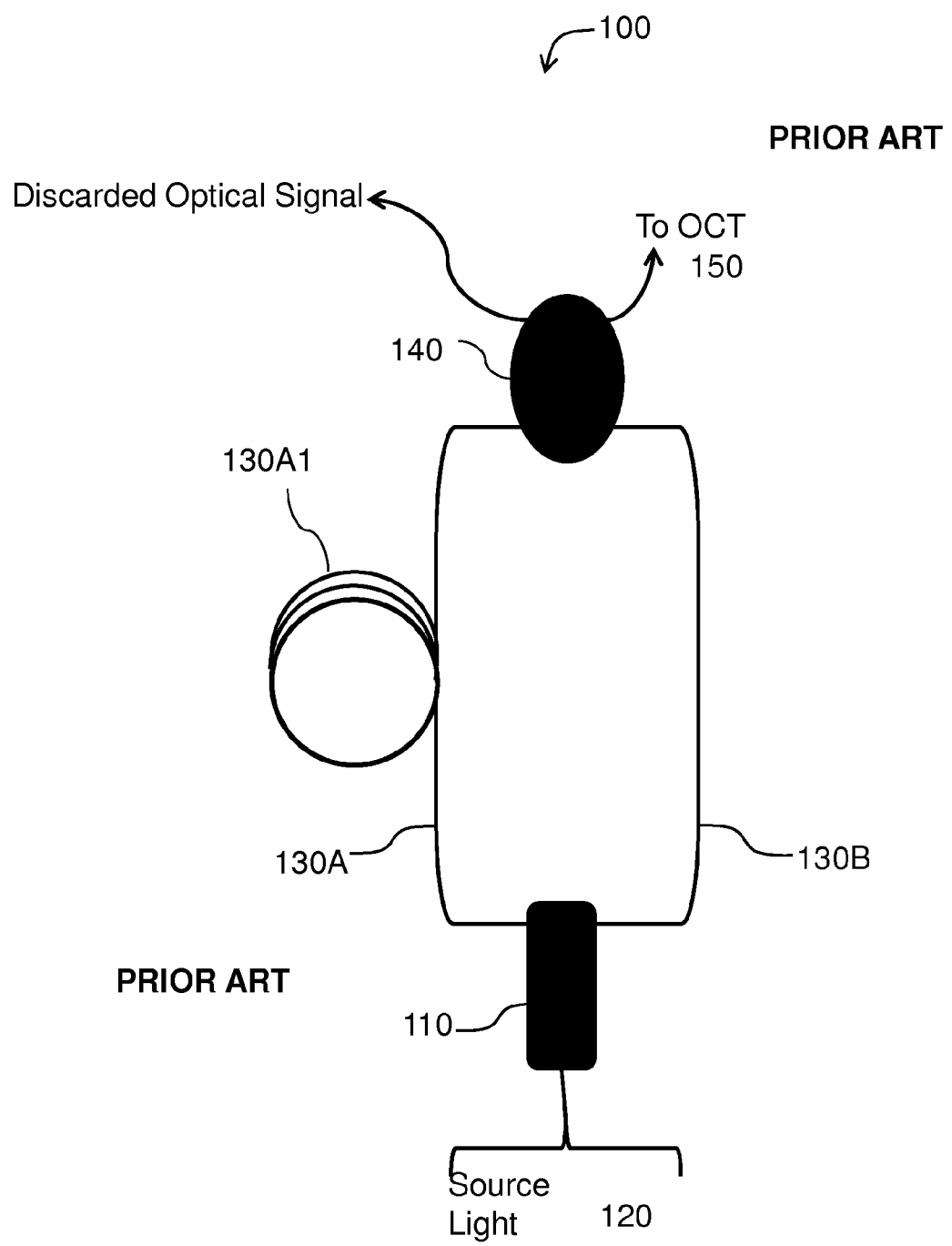
FIG. 1 illustrates a conventional optical buffering circuit.

The present invention provides optical circuits and methods for eliminating or reducing power loss in optical buffering. The invention utilizes an optical switch to recombine optical signals from multiple optical paths in a sequential manner to a single output. In certain aspects, the invention encompasses an optical circuit comprising a first optical path, a second optical path, and a means for recombining an optical signal transmitted through the first optical path with a signal transmitted through the second optical path by sequentially gating the first optical path and the second optical path to a single output. In other aspects, the invention comprises a method for reducing power loss in an optical circuit comprising transmitting an optical signal through a first optical path, transmitting an optical signal through a second optical path, and recombining the optical signals of the first and second paths by sequentially gating the first and second optical path to a single channel, thereby reducing power loss in the optical circuit. A conventional optical buffering circuit comprising a 2× buffer stage is depicted in FIG. 1. The circuit 100 comprises a 50/50 optical splitter 110 with one input port connected to a light source 120 and two output ports connected to a first and second optical fiber 130A and 130B. The first optical fiber 130A is longer than the second 130B such that light transmitted through the first optical fiber incurs a time delay relative to light transmitted through the second optical fiber. The additional length of the first optical fiber 130A is represented by the spooling of the fiber 130A1. Light from the first and second optical fibers 130A and 130B is recombined using a 2×2 50/50 coupler 140 with each output port of the coupler 140 containing only half the power from each input leg 130A and 130B. One of the output ports of the coupler 140 is then fed to the input/source arm of the OCT interferometer 150 and the other output port is discarded (i.e., not used by the OCT interferometer). The conventional optical buffering circuit 100 essentially discards half the optical power because it is not available in a single output port. This is disadvantageous because optical power in the native light source is limited to begin with.

Typically, relative time delay between the first and second optical fibers is adjusted to half of the period of the native A-line rate (e.g., imaging speed) of the light source and the duty cycle (i.e., the percentage of "on time") of the native light source is less than 50%. If 4× buffering is used, the duty cycle would be less than 25%, and so on for higher buffering orders. The light in the long segment and the light in the short segment is T/2 out of phase (where T is the repetition period of the native light source) and arrives at different times to the coupler in a non-overlapping manner.

Optical circuits of the invention replace the passive 50/50 optical coupler with an active optical switch, such as a 2×1 optical switch. The optical switch of the invention may be electronically toggled, for example, via an applied drive voltage, at a frequency and phase synchronized to the period of the native light source. The switch redirects light from either of the two input ports into a single output port in a sequential fashion, thereby avoiding the 50% optical loss associated with the use of 50/50 couplers in conventional optical buffering circuits.

Figure 2:
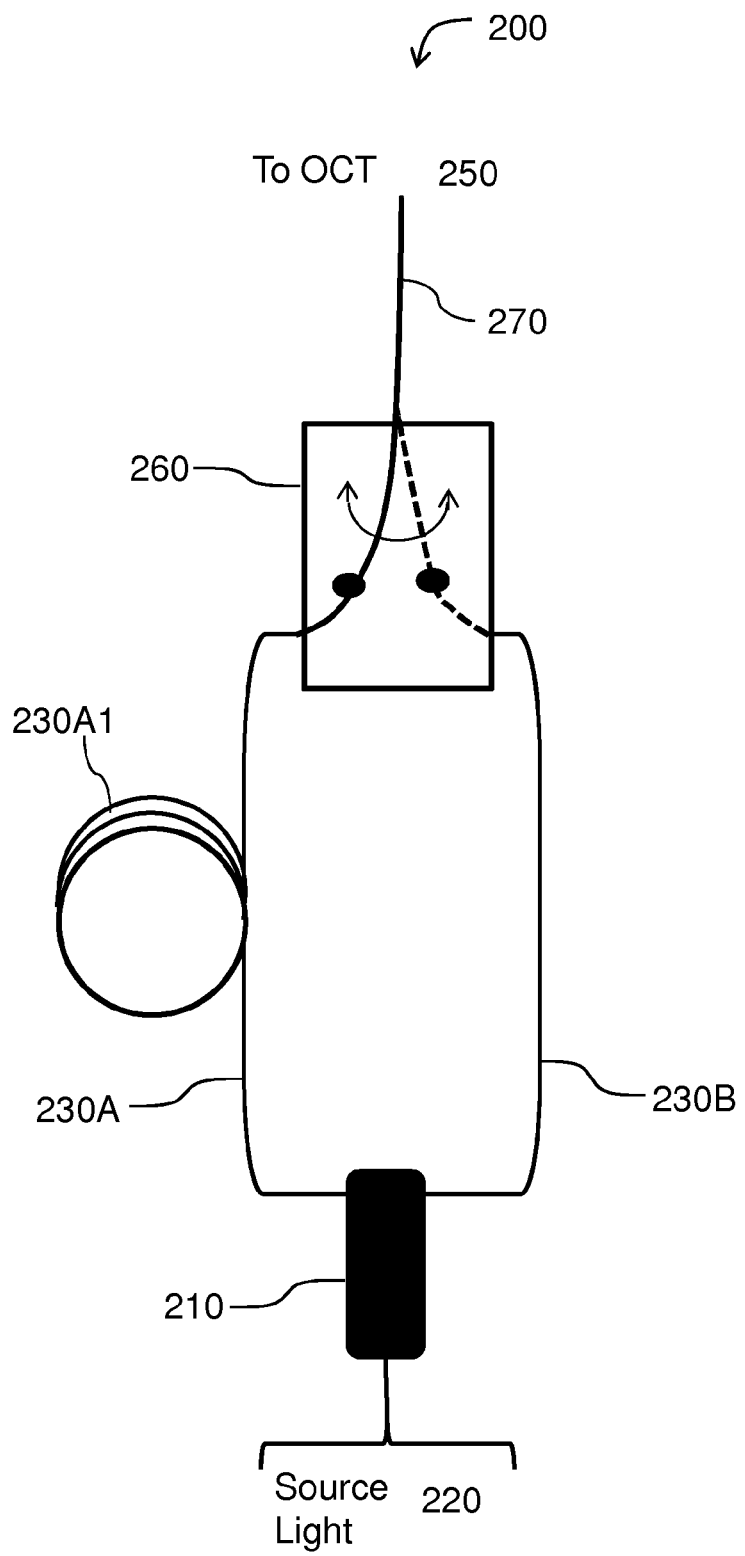
FIG. 2 illustrates an optical buffering circuit in accordance with the invention.

An exemplary optical circuit in accordance with the invention is provided in FIG. 2. The circuit 200 comprises a 50/50 optical splitter 210 with one input port connected to a light source 220 and two output ports connected to a first and second optical fiber 230A and 230B. The first optical fiber 230A is longer than the second 230B such that light transmitted through the first optical fiber 230A incurs a time delay relative to light transmitted through the second optical fiber 230B. The additional length of the first optical fiber 230A is represented by the spooling of the fiber 230A1. Light from the first and second optical fibers 230A and 230B is recombined using a 2×1 optical splitter 260 with an input port connected to each optical fiber 230A and 230B and an output port connected to an output channel 270. The optical switch 270 is electronically toggled between the first and second input ports such that optical signals from the first and second optical fiber 230A and 230B are recombined in a single port with none of the optical power being discarded. Accordingly, 100% of the power can be directed towards the OCT interferometer 250, rather than 50%.

Optical switches are well-known in the art. An optical switch is a switch that enables signals in optical fibers to be selectively switched from one circuit to another. An optical switch may operate by mechanical means, such as physically shifting an optical fiber to drive one or more alternative fibers, or by electro-optic effects, magneto-optic effects, or other methods. Slow optical switches, such as those using moving fibers, may be used for alternate routing of an optical switch transmission path. Fast optical switches, such as those using electro-optic or magneto-optic effects, may be used for various imaging methodologies. Any optical switch may be used in accordance with the invention. In preferred aspects of the invention, the optical switch is a fast optical switch. In some aspects of the invention, the optical switch is a passive optical switch. In preferred embodiments of the invention, however, the optical switch is an active optical switch. In this aspect, the toggling between the input ports of the switch can be actively controlled. In certain embodiments, the active optical switch is electronically toggled via an applied drive voltage at a frequency and phase synchronized to the period of the native light source. In certain embodiments of the invention, the optical switch is a 2×1 optical switch, such as the 1×2 MEMS PRO8 Series Optical Switch Module (Model No. OSW8102) available from Thorlabs, Inc. The invention is not limited to only 2×1 optical switches and can include 4×1 optical switches, 8×1 optical switches, and so forth, in addition to 2×1 optical switches. The selected optical switch can be adjusted as needed and depends on the buffering scheme implemented (i.e., a 2× buffering scheme, 4× buffering scheme, 8× buffering scheme, etc.). Accordingly, the invention comprises buffering approaches with higher multiplication factors (i.e., 4×, 8×, 16×, etc.). This may also raise the number of optical paths beyond simply a first and second optical path as necessary.

Like optical switches, optical splitters are also well-known in the art. An optical splitter is device that splits a beam of light into two or more beams. Any optical splitter may be used with the invention. In certain embodiments, the splitter is a 1×2 optical splitter. In further embodiments of the invention, the optical splitter is a 1×2 50/50 optical splitter. Any optical signal split ratio may be used. For example, while preferred embodiments of the invention utilize 50/50 split ratios, other ratios such as 90:10, 80:20, and 60:40 are also encompassed. In addition, 1×4, 1×8, and higher splitting schemes can be used depending on the contemplated optical buffering circuit. No matter the configuration, however, light from the different optical paths is recombined into a single output by redirecting light from any of the optical paths in a sequential fashion to a single output, preferably via an optical switch.

Any optical fiber may be used in accordance with the present invention. An optical fiber is a thin, flexible, transparent fiber made of glass or plastic that functions as a waveguide, or "light pipe" to transmit light between the two ends of the fiber. Optical fibers typically include a transparent core surrounded by a transparent cladding material with a lower index of refraction. Light is kept in the core by total internal reflection, which causes the fiber to act as a waveguide. Any optical fiber may be used in accordance with the invention. In certain aspects, the optical fiber is a single-mode optical fiber.

The invention may also encompass the use of polarization-maintaining optical fibers for use in polarization-maintaining buffering schemes. In fiber optics, polarization-maintaining optical fiber (PMF or PM fiber) is optical fiber in which the polarization of linearly polarized light waves launched into the fiber is maintained during propagation, with little or no cross-coupling of optical power between the polarization modes. Such fiber is used in special applications where preserving polarization is essential. Polarization maintaining optical fibers are well-known in the art, for example, the PANDA PM optical fiber, available from Fujikura, Ltd. Polarization-maintaining couplers may also be used in conjunction with the PM optical fibers for recombining optical signals from the PM optical fibers. Suitable PM couplers are also well-known in the art and can be commercially obtained, for example, from Thorlabs, Inc. (Model No. PMC780-50B-APC—1×2 PM Coupler). Circuits and methods of the invention are also useful with a variety of delay approaches, such as single-pass, double-pass, and quad-pass delay schemes. These delay schemes are also well-known in the art.

An exemplary assembly of a buffering circuit in accordance with the invention will now be provided. The source light is provided by a laser (Axsun Technologies ECTL) with a central wavelength of 1040 nm and a repetition rate of 100 kHz. The total tuning bandwidth is 110 nm, 100 nm of which is tuned during the sampling duty cycle. Because the switch is operated in the dead-time between the original and buffered sweeps, the entire 100 nm bandwidth is conserved for both the original (non-delayed) and buffered (delayed) sweeps. The sampling and laser-on duty-cycles are 46% and 62% respectively. A 60/40 splitter is used to compensate the 1.5 dB attenuation (70% transmission) of the fiber spool, such that both the original and buffered sweeps have similar power. The spool itself consists of 1000 m of HI1060 fiber. Three polarization controllers are used to adjust the polarization at the input of the fiber spool and at both inputs to the optical switch. The optical switch is commercially available (Boston Applied Technologies, based on their Nanona FOS platform). The switch employs transparent electro-optic ceramics to produce a variable wave plate, which is then used to produce a polarization independent 2×2 optical switch. The use of the switch improves buffer stage efficiency significantly compared to buffer stages that use 50/50 couplers to recombine optical signals, with considerably less loss of optical signal.

Optical circuits of the present invention can operate as a light source for a variety of uses, including imaging applications. In certain aspects, the light leaving the provided optical circuit is directed to an OCT system. Systems and methods of the invention are particularly amenable for use in OCT as the provided systems and methods can improve image quality and signal-to-noise.

Measuring a phase change in one of two beams from a coherent light is employed in optical coherence tomography. Commercially available OCT systems are employed in diverse applications, including art conservation and diagnostic medicine, e.g., ophthalmology. Recently, it has also begun to be used in interventional cardiology to help diagnose coronary heart disease. OCT systems and methods are described in U.S. Pat. Nos. 8,989,849; 8,531,676; 8,125,648; and 7,929,148, and U.S. Patent Application No. 2009/0043191, the contents of which are hereby incorporated by reference in their entirety.

Various lumen of biological structures may be imaged with the aforementioned imaging technologies in addition to blood vessels, including, but not limited to, vasculature of the lymphatic and nervous systems, various structures of the gastrointestinal tract including lumen of the small intestine, large intestine, stomach, esophagus, colon, pancreatic duct, bile duct, hepatic duct, lumen of the reproductive tract including the vas deferens, vagina, uterus, and fallopian tubes, structures of the urinary tract including urinary collecting ducts, renal tubules, ureter, bladder, and structures of the head, neck, and pulmonary system including sinuses, parotid, trachea, bronchi, and lungs.

In OCT, a light source delivers a beam of light to an imaging device to image target tissue. Within the light source is an optical amplifier and an tunable filter that allows that allows a user to select a wavelength of light to be amplified. Wavelengths commonly used in medical applications include near-infrared light, for example, 800 nm for shallow, high-resolution scans or 1700 nm for deep scans.

Generally, there are two types of OCT systems, common beam path systems and differential beam path systems, which differ from each other based upon the optical layout of the systems. A common beam path system sends all produced light through a single optical fiber to generate a reference signal and a sample signal, whereupon a differential beam path system splits the produced light such that a portion of the light is directed to the sample and the other portion is directed to a reference surface. The reflected light from the sample is recombined with the signal from the reference surface of detection. Common beam path interferometers are further described in, for example, U.S. Pat. Nos. 7,999,938; 7,995,210; and 7,787,127, the contents of which are incorporated by reference herein in its entirety.

In a differential beam path system, amplified light from a light source is inputted into an interferometer with a portion of light directed to a sample and the other portion directed to a reference surface. A distal end of an optical fiber is interfaced with a catheter for interrogation of the target tissue during a catheterization procedure. The reflected light from the tissue is recombined with the signal from the reference surface, forming interference fringes that allow precise depth-resolved imaging of the target tissue on a micron scale. Exemplary differential beam path interferometers are further described in, for example, U.S. Pat. Nos. 6,134,003; and 6,421,164, the contents of which are incorporated by reference herein in its entirety.

Figure 3:
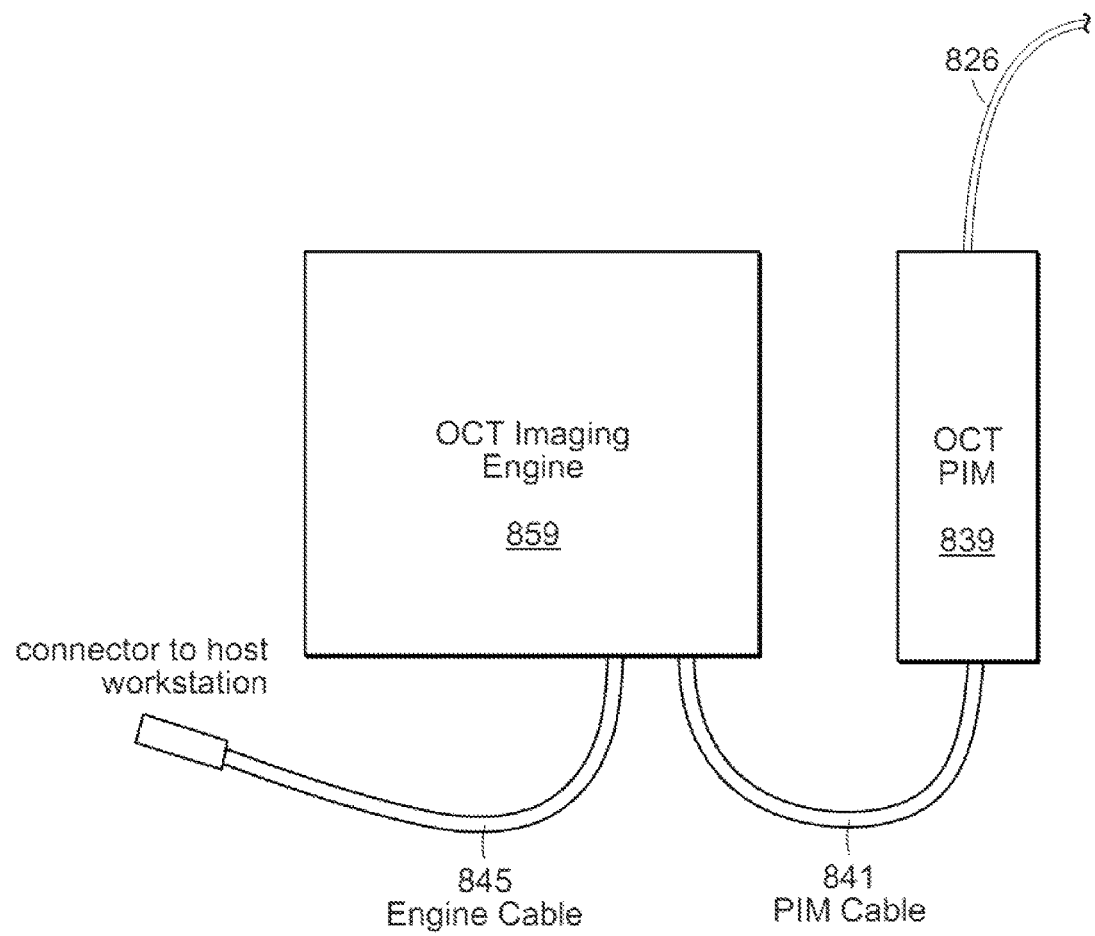
FIG. 3 is a diagram of components of an OCT subsystem.
Figure 4:
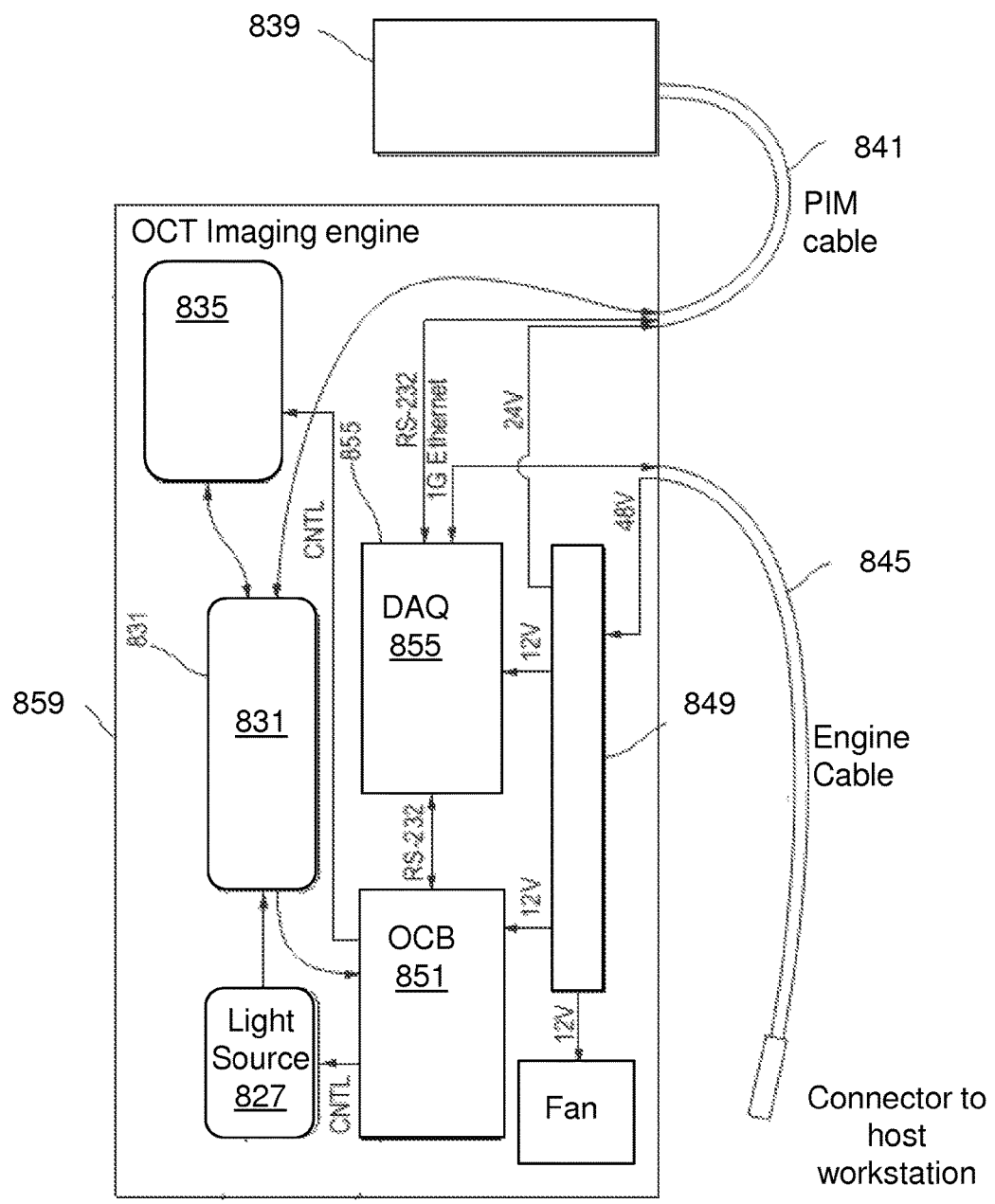
FIG. 4 is a diagram of the imaging engine shown in FIG. 3.

In embodiments using OCT, the system 700 will additionally comprise an OCT subsystem, depicted in FIGS. 3 and 4. Generally, an OCT system comprises three components which are 1) an imaging catheter 2) OCT imaging hardware, 3) host application software. When utilized, the components are capable of obtaining OCT data, processing OCT data, and transmitting captured data to a host system. OCT systems and methods are generally described in Milner et al., U.S. Pat. No. 8,989,849, Condit et al., U.S. Pat. No. 8,531,676 Castella et al., U.S. Patent Application Publication No. 2009/0043191, Milner et al., U.S. Pat. No. 8,125,648 and Kemp, N., U.S. Pat. No. 7,929,148 the content of each of which is incorporated by reference in its entirety. In certain embodiments, systems and methods of the invention include processing hardware configured to interact with more than one different three dimensional imaging system so that the tissue imaging devices and methods described here in can be alternatively used with OCT, IVUS, or other hardware.

In OCT, a light source delivers a beam of light to an imaging device to image target tissue. Light sources can be broad spectrum light sources, or provide a more limited spectrum of wavelengths, e.g., near infra-red. The light sources may be pulsed or continuous wave. For example the light source may be a diode (e.g., super-luminescent diode), or a diode array, a semiconductor laser, an ultra-short pulsed laser, or super-continuum light source. Typically the light source is filtered and allows a user to select a wavelength of light to be amplified. Wavelengths commonly used in medical applications include near-infrared light, for example between about 800 nm and about 1700 nm. Methods of the invention apply to image data obtained from obtained from any OCT system, including OCT systems that operate in either the time domain or frequency (high definition) domain.

In time-domain OCT, an interference spectrum is obtained by moving a scanning optic, such as a reference mirror, longitudinally to change the reference path and match multiple optical paths due to reflections of the light within the sample. The signal giving the reflectivity is sampled over time, and light traveling at a specific distance creates interference in the detector. Moving the scanning mechanism laterally (or rotationally) across the sample produces reflectance distributions of the sample (i.e., an imaging data set) from which two-dimensional and three-dimensional images can be produced.

In frequency domain OCT, a light source capable of emitting a range of optical frequencies passes through an interferometer, where the interferometer combines the light returned from a sample with a reference beam of light from the same source, and the intensity of the combined light is recorded as a function of optical frequency to form an interference spectrum. A Fourier transform of the interference spectrum provides the reflectance distribution along the depth within the sample.

Several methods of frequency domain OCT are described in the literature. In spectral-domain OCT (SD-OCT), also sometimes called "Spectral Radar" (Optics Letters, vol. 21, No. 14 (1996) 1087-1089), a grating or prism or other means is used to disperse the output of the interferometer into its optical frequency components. The intensities of these separated components are measured using an array of optical detectors, each detector receiving an optical frequency or a fractional range of optical frequencies. The set of measurements from these optical detectors forms an interference spectrum (Smith, L. M. and C. C. Dobson, Applied Optics vol. 28: (1989) 3339-3342), wherein the distance to a scatterer is determined by the wavelength dependent fringe spacing within the power spectrum. SD-OCT has enabled the determination of distance and scattering intensity of multiple scatters lying along the illumination axis by analyzing the exposure of an array of optical detectors so that no scanning in depth is necessary. Alternatively, in swept-source OCT, the interference spectrum is recorded by using a source with adjustable optical frequency, with the optical frequency of the source swept through a range of optical frequencies, and recording the interfered light intensity as a function of time during the sweep. An example of swept-source OCT is described in U.S. Pat. No. 5,321,501.

Time- and frequency-domain systems can further vary based upon the optical layout of the systems: common beam path systems and differential beam path systems. A common beam path system sends all produced light through a single optical fiber to generate a reference signal and a sample signal whereas a differential beam path system splits the produced light such that a portion of the light is directed to the sample and the other portion is directed to a reference surface. Common beam path systems are described in U.S. Pat. No. 7,999,938; U.S. Pat. No. 7,995,210; and U.S. Pat. No. 7,787,127 and differential beam path systems are described in U.S. Pat. No. 7,783,337; U.S. Pat. No. 6,134,003; and U.S. Pat. No. 6,421,164, the contents of each of which are incorporated by reference herein in their entireties.

In certain embodiments, the invention provides a differential beam path OCT system with intravascular imaging capability as illustrated in FIG. 3. For intravascular imaging, a light beam is delivered to the vessel lumen via a fiber-optic based imaging catheter 826, which is a multifunction catheter of the invention. The imaging catheter is connected through hardware to software on a host workstation. The hardware includes imagining engine 859 and a handheld patient interface module (PIM) 839 that includes user controls. The proximal end of imaging catheter 826 is connected to PIM 839, which is connected to imaging engine 859 as shown in FIG. 8A.

An embodiment of imaging engine 859 is shown in FIG. 4. Imaging engine 859 (i.e., the bedside unit) houses power distribution board 849, light source 827, interferometer 831, and variable delay line 835 as well as a data acquisition (DAQ) board 855 and optical controller board (OCB) 851. PIM cable 841 connects imagining engine 859 to PIM 839 and engine cable 845 connects imaging engine 859 to the host workstation (not shown). Light source 827 can be, in certain aspects, an optical circuit in accordance with the present invention. The light source 827, for example, can comprise the exemplary optical circuit depicted in FIG. 2. In this aspect, light leaving the output port of the optical switch is directed to the optical fiber interferometer 831 of the OCT system depicted in FIG. 4.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. An intravascular optical coherence tomography (OCT) imaging apparatus, comprising:
   a catheter or guidewire configured to be positioned within a blood vessel of a patient, the catheter or guidewire comprising an optical fiber configured to deliver light to the blood vessel to image the blood vessel;
   a system configured to generate an OCT image of the blood vessel and in communication with the catheter or guidewire, the system comprising an optical circuit configured to provide the light to the optical fiber via an output channel, the optical circuit comprising:
     a first optical path transmitting a first optical signal;
     a second optical path transmitting a second optical signal; and
     a means for recombining the first optical signal with the second optical signal without discarding an optical power of the first optical signal or the second optical signal, the means for recombining comprising a single output in communication with the output channel, wherein the means for recombining is configured to sequentially switch a connection of the first optical path and a connection of the second optical path to the single output such that the entire first optical signal and the entire second optical signal is sequentially directed to the output channel,
   wherein the system is configured to generate the OCT image based on the optical power of the entire first optical signal and the entire second optical signal.

2. The intravascular OCT imaging apparatus of claim 1, wherein the first optical path is longer than the second optical path.

3. The intravascular OCT imaging apparatus of claim 1, wherein the first optical signal is delayed relative to the second optical signal.

4. The intravascular OCT imaging apparatus of claim 1, wherein the means for recombining comprise an optical switch.

5. The intravascular OCT imaging apparatus of claim 4, wherein the optical switch comprises a 2.times.1 optical switch.

6. The intravascular OCT imaging apparatus of claim 1, wherein the optical circuit further comprises an optical splitter configured to split an optical signal from a light source between the first optical path and the second optical path.

7. The intravascular OCT imaging apparatus of claim 6, wherein the optical splitter comprises a 1.times.2 optical splitter.

8. The intravascular OCT imaging apparatus of claim 1, wherein the first and second optical paths comprise single mode optical fibers.

9. The intravascular OCT imaging apparatus of claim 1, wherein the first and second optical paths comprise polarization maintaining optical fibers.

10. The intravascular OCT imaging apparatus of claim 9, wherein the means for recombining comprise a polarization maintaining optical switch.

11. The intravascular OCT imaging apparatus of claim 1, wherein the means for recombining comprises an electro-optic switch configured to sequentially switch the connection of the first optical path and the connection of the second optical path to the single output.

12. The intravascular OCT imaging apparatus of claim 1, wherein the means for recombining comprises a magneto-optic switch configured to sequentially switch the connection of the first optical path and the connection of the second optical path to the single output.

13. The intravascular OCT imaging apparatus of claim 6, wherein the means for recombining is configured to sequentially switch the connection of the first optical path and the connection of the second optical path to the single output based on a voltage signal including a frequency and a phase, the frequency and phase synchronized to a periodicity of the light source.

14. The intravascular OCT imaging apparatus of claim 2, wherein the first optical signal comprises a buffered optical signal in swept-source OCT imaging, and wherein the second optical signal comprises a non-buffered optical signal in the swept-source OCT imaging.

* * * * *